(12) United States Patent
Luhmann et al.

(10) Patent No.: US 12,728,520 B2
(45) Date of Patent: Sep. 8, 2026

(54) HAND EXOSKELETON FOR REHABILITATION AND ASSISTANCE OF HAND MOTOR FUNCTIONS

(71) Applicant: ECOLE POLYTECHNIQUE FEDERALE DE LAUSANNE (EPFL), Lausanne (CH)

(72) Inventors: Ole Luhmann, Lausanne (CH); Luca Randazzo, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 555 days.

(21) Appl. No.: 18/022,432

(22) PCT Filed: Aug. 20, 2021

(86) PCT No.: PCT/IB2021/057675

§ 371 (c)(1),
(2) Date: Feb. 21, 2023

(87) PCT Pub. No.: WO2022/043843

PCT Pub. Date: Mar. 3, 2022

(65) Prior Publication Data

US 2023/0321814 A1 Oct. 12, 2023

(30) Foreign Application Priority Data

Aug. 22, 2020 (EP) .................................... 20192284

(51) Int. Cl.
*B25J 9/00* (2006.01)
*A61F 5/01* (2006.01)
*B25J 9/10* (2006.01)

(52) U.S. Cl.
CPC ............. *B25J 9/0006* (2013.01); *A61F 5/013* (2013.01); *B25J 9/1045* (2013.01)

(58) Field of Classification Search
CPC ........ B25J 9/0006; B25J 9/1045; A61F 5/013; A61F 2/586; A61H 2201/165
See application file for complete search history.

(56) References Cited

U.S. PATENT DOCUMENTS 2,545,452 A * 3/1951 Fletcher .................. A61F 2/586 623/64
5,178,137 A * 1/1993 Goor ..................... A61F 5/0111 601/40

(Continued)

FOREIGN PATENT DOCUMENTS

CN 110 731 880 1/2020
GB 2488760 A * 9/2012 ............... A61F 2/78

(Continued)

OTHER PUBLICATIONS

International Search Report dated Dec. 23, 2021, for PCT/IB2021/057675, 3 pp.

(Continued)

*Primary Examiner* — Brandy S Lee
*Assistant Examiner* — Mishal Zahra Hussain
(74) *Attorney, Agent, or Firm* — NIXON & VANDERHYE

(57) ABSTRACT

A device and system for e.g. rehabilitation and assistance of hand motor functions, in particular a portable and under-actuated hand exoskeleton for use in activities of daily living, is disclosed.

21 Claims, 8 Drawing Sheets

(56) References Cited

U.S. PATENT DOCUMENTS

| | | | | |
|---|---|---|---|---|
| 8,235,928 | B2 * | 8/2012 | Padova | A61F 5/0118 602/5 |
| 10,449,677 | B1 * | 10/2019 | Al Najjar | B25J 9/0006 |
| 11,672,721 | B2 * | 6/2023 | Sankai | A61H 1/0288 601/5 |
| 2006/0224249 | A1 * | 10/2006 | Winfrey | A61F 2/70 623/64 |
| 2010/0041521 | A1 | 2/2010 | Ingvast et al. | |
| 2013/0072829 | A1 * | 3/2013 | Fausti | A63B 21/4035 601/40 |
| 2013/0219585 | A1 | 8/2013 | Bergelin et al. | |
| 2016/0015590 | A1 | 1/2016 | Arata et al. | |
| 2016/0361179 | A1 | 12/2016 | Mateus Dias Quinaz | |
| 2019/0015233 | A1 * | 1/2019 | Galloway | B25J 15/12 |
| 2020/0324402 | A1 * | 10/2020 | Roh | A61H 1/00 |
| 2020/0345575 | A1 | 11/2020 | Randazzo et al. | |
| 2023/0263644 | A1 * | 8/2023 | Sankai | A61F 2/586 623/64 |

FOREIGN PATENT DOCUMENTS

| | | | | |
|---|---|---|---|---|
| KR | 101740310 | B1 * | 5/2017 | B25J 9/0006 |
| WO | WO-2013012029 | A1 * | 1/2013 | A61F 2/583 |
| WO | WO-2015134336 | A2 * | 9/2015 | A61B 5/0022 |
| WO | 2017/072463 | | 5/2017 | |
| WO | 2019/103538 | | 5/2019 | |

OTHER PUBLICATIONS

Written Opinion of the ISA dated Dec. 23, 2021, for PCT/IB2021/057675, 7 pp.

"RELab tenoexo: A Robotic Hand Orthosis for Therapy and Assistance in Activities of Daily Living", ETH Zurich, ETH Zurich, accessed Oct. 24, 2025, pp. 1-8.

Birglen et al., "1 Introduction", Underactuated Robotic Hands, by Lionel Birglen, Thierry Laliberté, and Clément M. Gosselin, STAR 40, Springer-Verlag Berlin Heidelberg, 2008, p. 1.

Bonita et al., "Recovery of Motor Function After Stroke", Stroke, vol. 19, Vo. 12, Dec. 1988, pp. 1497-1500.

Bos et al., "A structured overview of trends and technologies used in dynamic hand orthoses", Journal of NeuroEngineering and Rehabilitation, vol. 13, No. 62, 2016, pp. 1-25.

Bützer et al. "Fully Wearable Actuated Soft Exoskeleton for Grasping Assistance in Everyday Activities", Soft Robotics, 2020, pp. 1-16.

Cook et al., "Deriving Weights from Pairwise Comparison Ratio Matrices: An Axiomatic Approach", European Journal of Operational Research, vol. 37, No. 3, 1988, pp. 355-362.

Derler et al., "Friction of Human Skin against Smooth and Rough Glass as a Function of the Contact Pressure", Tribology International, vol. 42, No. 11-12, 2009, pp. 1565-1574.

Dick et al., "Introduction", Requirements Engineering, 2017, pp. 1-32.

Dollar, "Classifying Human Hand Use and the Activities of Daily Living", The Human Hand as an Inspiration for Robot Hand Development, Springer, 2014, pp. 201-216.

Doyle, "Anatomy of the Finger Flexor Tendon Sheath and Pulley System", The Journal of Hand Surgery, vol. 13, No. 4, Jul. 1988, pp. 473-484.

Drake et al., "Skin and Fascias", Gray's Anatomy for Students, 2nd ed., 2010, pp. 41-42.

Geisler et al., "Recovery of Motor Function after Spinal-Cord Injury: A Randomized, Placebo-Controlled Trial with GM-1 Ganglioside", New England Journal of Medicine, vol. 324, No. 26, Jun. 27, 1991, pp. 1829-1838.

Gordon et al., "Hand Length", Anthropometric Survey of US Army Personnel: Interim Report for 1988, Extract, pp. 190-191.

Greiner, "Hand Anthropometry of US Army Personnel", Dec. 1991, extract, pp. 1-10.

Heo et al., "Current Hand Exoskeleton Technologies for Rehabilitation and Assistive Engineering", International Journal of Precision Engineering and Manufacturing, vol. 13, No. 5, May 2012, pp. 807-824.

Hofmann et al. "Design and Evaluation of a Bowden-Cable-Based Remote Actuation System for Wearable Robotics", IEEE Robotics and Automation Letters, vol. 3, No. 3, Feb. 2018, pp. 1-8.

Howell, "Introduction to Compliant Mechanisms", Handbook of Compliant Mechanisms, 2013, Extract, pp. 1-3.

Ivanhoe et al., "Spasticity: The Misunderstood Part of the Upper Motor Neuron Syndrome", American Journal of Physical Medicine & Rehabilitation, vol. 83, Oct. 2004, pp. S3-S9.

Jacobson et al., "Neuroanatomy for the Neuroscientist", 2018, pp. 138-140.

Lambercy et al., "Robot-assisted Rehabilitation of Hand Function", Rehabilitation Robotics, 2018, pp. 205-225.

Lee et al., "Ergonomic Evaluation of Biomechanical Hand Function", Safety and Health at Work, vol. 6, No. 1, Mar. 2015, pp. 9-17.

Lee et al., "Transmission of Musculotendon Forces to the Index Finger", The Human Hand as an Inspiration for Robot Hand Development, Springer, 2014, pp. 49-75.

Lewitt, "Clonus", Encyclopedia of the Neurological Sciences, 2nd ed., Elsevier Inc, 2014, pp. 728-729.

Marcus et al., Integrated Neuroscience: A Clinical Problem Solving Approach, Springer Science, extract, 2003, p. 1.

Matheus et al., "Benchmarking Grasping and Manipulation: Properties of the Objects of Daily Living." The 2010 IEEE/RSJ International Conference on Intelligent Robots and Systems, Oct. 18-22, 2010, pp. 5020-5027.

Mattson et al., "Product Development: Principles and Tools for Creating Desirable and Transferable Designs", Jan. 2020, pp. 3-8.

Milner et al., "Activation of Intrinsic and Extrinsic Finger Muscles in Relation to the Fingertip Force Vector", Experimental Brain Research, vol. 146, No. 2, Sep. 2002, pp. 197-204.

Mullerpatan et al., "Grip and Pinch Strength: Normative Data for Healthy Indian Adults", Hand Therapy, vol. 18, No. 1, Mar. 2013, pp. 11-16.

Nycz et al. "Design Criteria for Hand Exoskeletons: Measurement of Forces Needed to Assist Finger Extension in Traumatic Brain Injury Patients." IEEE Robotics and Automation Letters, vol. 3, No. 4, Oct. 2018, pp. 3285-3292.

Ogrodnik, "Medical Device Design: innovation from concept to market", Academic Press, 2013, pp. 1-9.

Pons et al., "Introduction to wearable robotics", Wearable Robots: Biomechatronic Exoskeletons, John Wiley & Sons, Ltd., 2008. pp. 1-2.

Quinn et al., "Amyotrophic Lateral Sclerosis and Other Motor Neuron Diseases", Continuum: Lifelong Learning in Neurology, vol. 26, No. 5, Oct. 2020, pp. 1323-1347.

Radder et al., "User-centred input for a wearable soft-robotic glove supporting hand function in daily life", 2015 IEEE International Conference on Rehabilitation Robotics (ICORR), 2015, pp. 502-507.

Randazzo et al., "mano: A Wearable Hand Exoskeleton for Activities of Daily Living and Neurorehabilitation." IEEE Robotics and Automation Letters, vol. 3, No. 1, Oct. 2017, pp. 1-8.

Richards et al., "People with spinal cord injury in the United States", American Journal of Physical Medicine & Rehabilitation, vol. 96, No. 2, Feb. 2017, pp. S124-S126.

Saaty, "Relative Measurement and Its Generalization in Decision Making: Why Pairwise Comparisons are Central in Mathematics for the Measurement of Intangible Factors The Analytic Hierachy/Network Process", Revista de la Real Academia de Ciencias Exactas, Físicas y Naturales. Serie A. Matemáticas (RACSAM), vol. 102, No. 2, 2008, pp. 251-318.

Sanger et al., "Classification and Definition of Disorders Causing Hypertonia in Childhood", Pediatrics, vol. 111, No. 1, 2003, pp. e89-e97.

Sasidharan, "Smart Glove: An Assistive Device to Enhance Recovery of Hand Function During Motor Rehabilitation", A Thesis Presented in Partial Fulfillment of the Requirements for the Degree Master of Science, Aug. 2015, pp. 1-62.

(56) References Cited

OTHER PUBLICATIONS

Shahid et al., "Moving toward Soft Robotics: A Decade Review of the Design of Hand Exoskeletons", Biomimetics, vol. 3, No. 3, Jul. 18, 2018, Article 17, pp. 1-20.
Siciliano et al., "Springer Handbook of Robotics", Springer, 2016, pp. 1-2.
Singer et al., "Chorea, Athetosis, and Ballism", Movement Disorders in Childhood, Second Edition, 2016, pp. 143-175.
Smaby et al., "Identification of Key Pinch Forces Required to Complete Functional Tasks", Journal of Rehabilitation Research & Development, vol. 41, No. 2, Mar./Apr. 2004, pp. 215-223.
Snoek et al. "Survey of the Needs of Patients with Spinal Cord Injury: Impact and Priority for Improvement in Hand Function in Tetraplegics", Spinal Cord, vol. 42, 2004, pp. 526-532.
Stack et al., "Occupational Ergonomics: A Practical Approach. 1st ed.", John Wiley & Sons, Inc., 2016, pp. 5-19.
Stillfried et al., "MRI-Based Skeletal Hand Movement Model", The Human Hand as an Inspiration for Robot Hand Development, Springer, 2014, pp. 1-14.
Tubiana, "The Hand", 1981, extract, pp. 1-3.
Virani et al., "Heart Disease and Stroke Statistics—2020 Update", Circulation, vol. 141, Mar. 3, 2020, pp. e139-e596.
Xu et al., "Design of a Highly Biomimetic Anthropomorphic Robotic Hand towards Artificial Limb Regeneration", 2016 IEEE International Conference on Robotics and Automation (ICRA), 2016, pp. 1-8.

* cited by examiner

HAND EXOSKELETON FOR REHABILITATION AND ASSISTANCE OF HAND MOTOR FUNCTIONS

CROSS-REFERENCE TO RELATED APPLICATIONS

This application is the U.S. national phase of International Application No. PCT/IB2021/057675 filed Aug. 20, 2021 which designated the U.S. and claims priority to EP 20192284.6 filed Aug. 22, 2020, the entire contents of each of which are hereby incorporated by reference.

TECHNICAL FIELD

The present invention relates to a device and system for e.g. rehabilitation and assistance of hand motor functions, in particular to a portable hand exoskeleton for use in activities of daily living.

BACKGROUND ART

Hand sensorimotor impairments are among the most common consequences of injuries affecting the central and peripheral nervous systems, leading to a drastic reduction in the quality of life for affected individuals. Hands are integral parts of the human body and serves assorted functions for minor and major activities. Grasping and manipulating are among the most frequently utilized abilities in activities of daily living (ADL) and in professional environments. Thus, the impairment of a hand results in far-reaching consequences for the impacted individual. The loss of upper-limb motor function is commonly linked with upper motor neuron (UMN) syndromes.

The upper motor neuron syndrome is a group of symptoms, which can be caused by a lesion of the corticospinal tract. The corticospinal tract spans from the brain down the spinal cord. Thus, an injury of the brain and/or spinal cord can lead to UMN syndrome. Spasticity, paralysis and muscle weakness are typical symptoms of UMN syndrome. Potential causes of UMN syndrome are: stroke, traumatic brain injury (TBI), cerebral palsy, spinal cord injury (SCI) and amyotrophic lateral sclerosis (ALS).

Medical rehabilitation of motor functions is usually performed in a hospital or the like in order to recover function lowered by disease or injury. In recent years, for the purposes of improving recovery of impaired functions, enabling quantitative evaluations of recovery or reducing the burden of rehabilitation workers, attempts have been made to apply wearable exoskeletal technologies to rehabilitation and assistance of motor functions. The use of wearable technologies has been proposed as a tool for restoring and complementing impaired motor functions for such users. By acting as complements of impaired human body's functions, these systems can be used to provide motor assistance or to promote recovery of functions, both inside healthcare centers and during activities of daily living. During the rehabilitation process robotic devices can form a complementary approach to traditional therapy by providing movement to the impaired limb while collecting data to evaluate the progress. Moreover, wearable and portable robotic devices, which strengthen the user's grasping force, can ease manipulation of objects during ADL.

However, despite these systems are commonly used in research laboratories and highly-specialized centers, they still suffer from an important limitation: their adoption by users on a daily basis is limited because of complexity, poor usability and high costs. Indeed, the translation of these systems to domestic settings could enable intensive and continuous use during meaningful activities of daily living, ultimately improving their effectiveness.

Several concepts of hand exoskeletons for motor rehabilitation and assistance purposes have been proposed in the past. For instance, US Patent Application 2016/0361179 discloses a device for actively and dynamically assist and lock joints, with low power consumption, small volume and light weight, having a supporting structure in the joint, at least one tensioning system fixed to the supporting structure and at least one artificial tendon connected to the tensioning system. The tension system interacts with the locking system in order to assist the user's joints when needed.

US Patent Application 2016/0015590 discloses a hand exoskeleton device that can be mounted onto a human body, and can operate a three-layered sliding spring mechanism serving as a motion transfer mechanism for applying drive power to a distal interphalangeal joint (DIP joint), a proximal interphalangeal joint (PIP joint) and a metacarpophalangeal joint (MP joint) using a single direct acting actuator, thereby supporting the gripping motions of the human body with the device mounted thereon.

US Patent Application 2013/0219585 discloses a grasp assist system including a glove, actuator assembly, and controller. The glove includes a digit, i.e., a finger or thumb, and a force sensor. The sensor measures a grasping force applied to an object by an operator wearing the glove. Phalange rings are positioned with respect to the digit. A flexible tendon is connected at one end to one of the rings and is routed through the remaining rings. An exoskeleton positioned with respect to the digit includes hinged interconnecting members each connected to a corresponding ring, and/or a single piece of slotted material. The actuator assembly is connected to another end of the tendon. The controller calculates a tensile force in response to the measured grasping force, and commands the tensile force from the actuator assembly to thereby pull on the tendon. The exoskeleton offloads some of the tensile force from the operator's finger to the glove.

US Patent Application 2013/0072829 discloses a flexible, modular and lightweight hand rehabilitation device comprising a brace fitted to partially cover the patient's hand and forearm, the device comprising, all placed on the back of the hand with the palm totally free, flexible rods for a passive and assisted active bending/extension of the five fingers, finger gloves provided with thimbles, fixed rods or plates stabilised to thimbles and hinged to one end of the flexible rods by means of a hinge and a quick coupling mechanism defining an articulated joint, a movement/command and control unit integral to the brace or remotely located relative to the same and provided with five actuating means for moving the flexible rods and further comprising means for adjusting the tension of said rods, means for adjusting and adapting the rehabilitation device to the hand's anatomical features and a control and management software.

US Patent Application 2010/0041521 discloses a finger glove for use in gripping movements with one or more fingers of a human hand enclosed in the glove. The glove includes glove fingers and a palm. At least one glove finger is adapted to include on each side an artificial tendon that extends along an inside of the glove. A yoke is fitted in a tip of the at least one glove finger and intended to surround a tip of an enclosed finger. At each side of the glove finger artificial tendons are connected to the yoke. A system including the finger glove having a force detecting sensor is situated on the inside of the at least one glove finger and is adapted to detect a force between a finger enclosed in the glove finger and a contact surface applied to the finger. The artificial tendons for a glove finger are connected to at least one actuator and a control unit adapted to cause the at least one actuator to exert a pulling force on the artificial tendons of the glove finger based on a force detected in the force detecting sensor, whereby the finger enclosed in the glove finger is caused to bend.

US Patent Application 2020/0345575 discloses a modular, orthosis-free hand exoskeleton device designed to be wearable, portable and light in weight, and comprising from one to ten modules each having an actuating mechanism such as a linear actuator coupled with an artificial tendon having a flexible cable or shaft encased into a sheath and an elastic, stretchable portion on its distal end.

All the above-mentioned hand exoskeletons present certain drawbacks or otherwise limitations, particularly when it comes to rehabilitation or use during activities of daily living. For instance, many of those devices are bulky, poorly usable and costly in view of their complexity. Some are not designed to be used outside of clinical settings and/or without any monitoring performed by a medical practitioner mainly because of their non-portability. Some devices do not allow to control both flexion and extension of fingers, and many of them do not preserve natural somatosensation on palms and fingertips. Others may not exert sufficient force on the impaired fingers to firmly grasp an object.

Moreover, the vast majority of the prior art devices comprise some kind of gloves. This aspect has the main advantage of facilitating the placement of sensors or actuating units on or close to the fingertips; however, gloves are extremely difficult to wear for patients who suffered from UMN. Indeed, these patients typically suffer from flaccid hands or contracted hands, and therefore have great difficulties in wearing glove garments, even e.g. winter gloves. This is due to two main problems. Flaccid hands make gloves difficult to wear because pushing a tone-less finger inside a closed sheath (such as the finger-sheath of a glove) typically leads to buckling of the finger itself—making it difficult to push all fingers inside the glove. On the other side, contracted fingers are difficult to open all the same time, which makes it difficult to align all them to the gloves sheaths and wear the gloves fingers. Overall, glove-based designs suffer from important limitations for UMN users—making their use highly impractical. Furthermore, glove-based designs keep the fingertips and/or the palm of the hand covered, hampering natural somatosensation during interactions with external objects and tools.

SUMMARY OF INVENTION

The present invention provides for a new kind of hand exoskeleton for rehabilitative and assistive purposes that addresses or at least reduces one or more of the above-mentioned drawbacks of the devices known in the art.

A main of aim of the invention is to provide for a fully wearable, portable and minimally obtrusive exoskeleton device and to improve the known devices.

Another aim of the invention is to provide for a hand exoskeleton that may control flexion-extension of the fingers, while allowing natural somatosensorial interactions with the environment surrounding the users.

Still a further aim of the invention is to provide for a hand exoskeleton adapted to assist and restore hand functions of users with motor disabilities both during activities of daily living and in neurorehabilitative scenarios.

Another aim of the invention is to provide for a hand exoskeleton autonomously and easily wearable by impaired users, accessible—and of easy manufacturing. All these aims have been accomplished with the device of the invention, as described hereinafter and in the appended claims. Accordingly, one object of the present invention relates to a hand exoskeleton according to claim 1.

In particular, a hand exoskeleton according to the invention comprises:

a) a hand-wearable support having a portion configured to be connected in proximity to a metacarpophalangeal (MCP) joint of a user; and b) an elongated motion unit operatively connected to, or stemming from, the hand-wearable support, said motion unit comprising:

i) a plurality of adjacent movable members located along the longitudinal axis of the motion unit, each movable member comprising a first and second cavity along its entire length;

ii) a compliant layer running through said motion unit and along the longitudinal axis of the motion unit;

iii) a first cable or wire running inside said first cavity and connected to the motion unit;

iv) a second cable or wire running inside said second cavity and connected to the motion unit;

v) at least one finger support configured to locate two fingers of a user wearing the exoskeleton wherein said motion unit is connected at one end to the finger support.

Named "proximal end" a first end of the elongated motion unit connected to, or stemming from, the hand-wearable support, and "distal end" the opposed end of the elongated motion unit along its longitudinal axis, the finger support is designed and conceived to be located at the distal end of the motion unit, and is sized and shaped to insert and accommodate two fingers of a user.

Additionally, the hand-wearable support is designed and conceived so that the proximal end of the elongated motion unit can be connected thereto, or stems from, in a position allowing said motion unit to be located between two fingers of a user when worn. In this way, the elongated motion unit results as an "additional finger" in between for instance an index and a middle finger, a middle finger and a ring finger, or a ring finger and a pinky finger.

In one embodiment, the motion unit comprises:

i) a first, top layer of adjacent partial movable members comprising a first cavity along its entire length;

ii) a second, bottom layer of adjacent partial movable members comprising a second cavity along its entire length;

iii) a compliant layer located, such as sandwiched, between said first, top layer and said second, bottom layer;

iv) a first cable or wire running inside said first cavity and connected to said first, top layer; and v) a second cable or wire running inside said second cavity and connected to said second, bottom layer wherein each partial movable member of said top layer faces a partial movable member of said bottom layer to define a complete movable member. The so-obtained movable member comprises a portion of the compliant element located/sandwiched between each partial movable member.

The device according to the invention relies on an elongated motion unit which employs actuating mechanisms and artificial tendons to control the fingers of the wearer. One of the main innovations of the hand exoskeleton of the present invention is the capability to actuate fingers opening and closing through a compliant mechanism devoid of any glove that (i) can generate forces compatible with use in ADL and physiologically-correct ranges of motions, (ii) is compliant for comfortable adaptability to different finger morphologies, and (iii) enables autonomous wearability by UMN patients. This is achieved thanks to the novel concept of the elongated motion unit—which can exchange forces with external objects at its tip (e.g. actively flex and extend fingers attached to it) while maintaining torsional stiffness. The latter is one of the main advantageous features of the hand exoskeleton disclosed herein—and it is achieved thanks to the inventive step described hereafter.

The elongated motion is composed by a segmented structure (as described in the rest of this document). The core operating principle of the structure is to be mechanically actuated by cables in order to flex/extend and exchange mechanical energy with external objects e.g. to control the flexion and extension of a human finger when used as an exoskeleton, or to grasp and hold items when used as a robotic gripper's finger. The structure is underactuated as it has less degrees of actuation than degrees of freedom.

Due to its segmented design and under-actuation, the structure is mechanically compliant. Compliance is a desirable feature when the structure is not actuated by the cables—enabling it, thanks to its flexibility, e.g. to be easily worn and to comply with different finger morphologies. Compliant structures, however, typically present undesirable limitations when they are actuated. In fact, when encountering a resisting force (e.g. the finger to be moved which acts as a mechanical load), these structures can typically discharge the energy provided by the actuation system along several axes and not only at their tip or along the main flexion-extension plane. The latter is not a desirable effect, as it reduces the energy that can be effectively exchanged with external objects, hence reducing the functionality of these structures (e.g. limiting the force that can be exchanged with human fingers to control their opening and closing). Depending on the amount of the resisting force encountered by the structure (e.g. which can be very high for these kind of structures in the case of contracted human fingers as typical in patients with UMN syndromes), the overall energy provided by the actuation unit could be fully dissipated in non-functional off-plane motions, resulting in very limited or no motions of the attached load (e.g. the wearer's finger).

The elongated motion unit of the invention solves the problem through a mechanical design that enables to maximize torsional stiffness while the structure is actuated, and prevents the structure to undesirably discharge mechanical energy on planes lying outside the fingers' flexion-extension plane. By mechanically coupling each elongated motion unit to two human fingers, the elongated motion unit enables to solve the inherent under-actuation problem when being actuated thanks to a dimensionality reduction of its degrees of freedom, and to the over-constraining of its motion on a plane which always lies parallel to the flexion-extension planes identified by the two coupled human fingers. Importantly, this enables to exploit already-existing mechanical structures (the human fingers themselves) as both functional devices enabling the operation of the structure and as users of the mechanical energy.

By exploiting the underlying mechanical structures of the fingers themselves, the design complexity of the elongated motion unit can be drastically reduced. Contrary to state-of-the-art devices for exoskeletal motion which typically solve at the device-level the design objectives of optimal force exchange (e.g. through torsionally stiff mechanical joints which result in bulky and poorly wearable systems) and optimal range of motion (through lever-based mechanical structures extending highly over the hand resulting in poor wearability and usability in daily living), the object of this invention enables to share the design complexity between the device itself and its load, the human fingers. The fingers—when coupled to the device of this invention—become indeed an integral structural part of its functioning, as they become carrier of the fundamental function of increasing torsional stiffness. Importantly, by sharing the design complexity between the device itself and the already existing human fingers, the elongated motion unit can achieve similar or better performance as its state-of-the-art counterparts but with a drastically reduced mechanical footprint. Specifically, thanks to its novelty, this invention enables to build hand exoskeletal systems with several advantages: (i) generate forces compatible with use in ADL and physiologically-correct ranges of motions, (ii) compliance for comfortable adaptability to different finger morphologies, and (iii) autonomous wearability by UMN patients to achieve physiologically-correct movements and forces that can support in activities of daily living. Overall, this enables the development of exoskeletal systems that allow comfortable and easy operations by patients themselves in their daily environments—to the benefits of increased intensity of operations (e.g. increased dose of functional therapy) in meaningful settings such as home, which are core tenets behind modern neurorehabilitation for UMN patients (see FIGS. 1, 7 and 14).

Furthermore, the elongated motion unit may be used to control fingers motions from the back side of the hand, freeing the wearer's palm and fingertips from hindrances in interaction with external objects and tools. This approach has the unique advantages of enabling, within a single wearable and portable device, control of fingers flexion and extension with preservation of natural somatosensation on palms and fingertips of the wearer, while at the same time improving the grasping performances.

Another object of the present invention relates to a hand exoskeleton system according to claim 9. The system comprises the hand exoskeleton described in the present disclosure operatively connected to a bi-directional actuating mechanism. The actuation mechanism, control and energy storage units may be placed for instance inside a chest-pack or a waist-pack. This allows users e.g. sitting on a wheelchair to comfortably rest their backs and shoulders against the backseats of their wheelchairs, enabling comfortable use of the system for prolonged periods.

Further embodiments of the present invention are defined by the appended claims.

The above and other objects, features and advantages of the herein presented subject-matter will become more apparent from a study of the following description with reference to the attached figures showing some preferred aspects of said subject-matter.

DETAILED DESCRIPTION OF THE INVENTION

Figure 1:
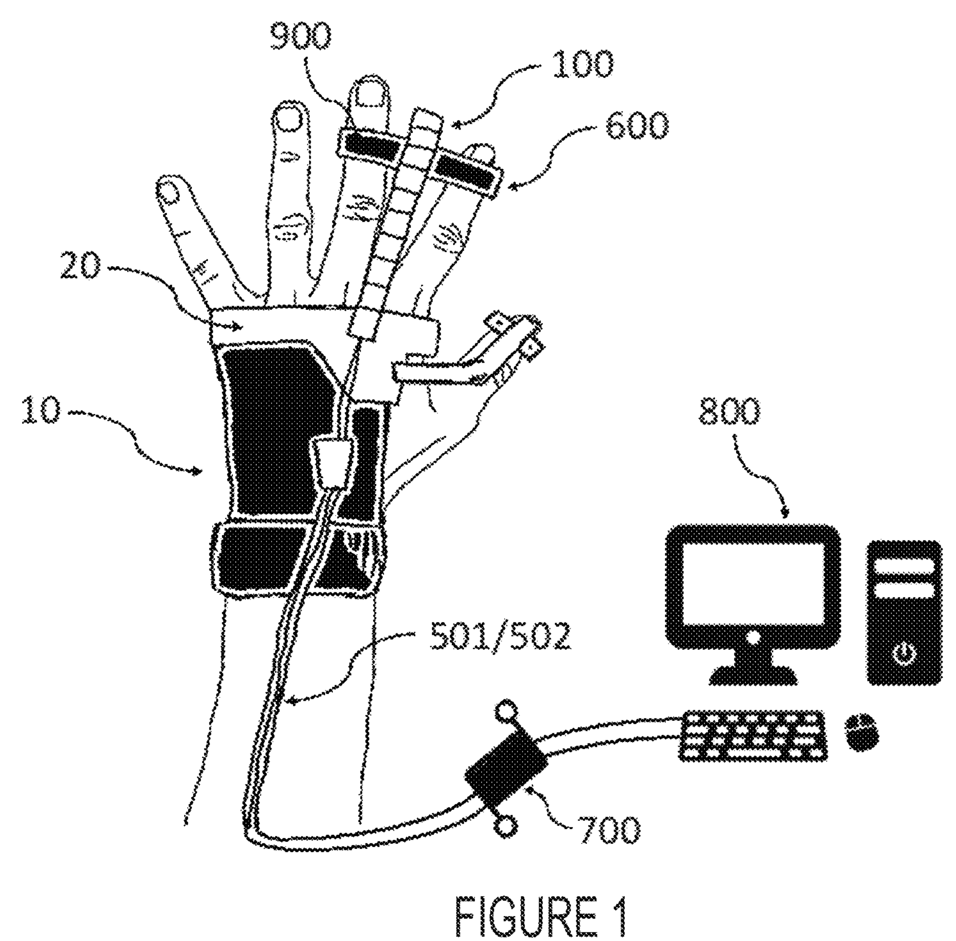
FIG. 1 depicts one embodiment of the system according to the invention.

The subject-matter described in the following will be clarified by means of a description of those aspects which are depicted in the drawings. It is however to be understood that the scope of protection of the invention is not limited to those aspects described in the following and depicted in the drawings; to the contrary, the scope of protection of the invention is defined by the claims. Moreover, it is to be understood that the specific conditions or parameters described and/or shown in the following are not limiting of the scope of protection of the invention, and that the terminology used herein is for the purpose of describing particular aspects by way of example only and is not intended to be limiting.

Unless otherwise defined, technical and scientific terms used herein have the same meaning as commonly understood by one of ordinary skill in the art to which this invention belongs. Further, unless otherwise required by the context, singular terms shall include pluralities and plural terms shall include the singular. The methods and techniques of the present disclosure are generally performed according to conventional methods well known in the art and as described in various general and more specific references that are cited and discussed throughout the present specification unless otherwise indicated. Further, for the sake of clarity, the use of the term "about" is herein intended to encompass a variation of +/−10% of a given value.

Non-limiting aspects of the subject-matter of the present disclosure will be described by way of example with reference to the accompanying figures, which are schematic and are not intended to be drawn to scale. For purposes of clarity, not every component is labelled in every figure, nor is every component of each aspect of the invention shown where illustration is not necessary to allow those of ordinary skill in the art to understand the invention.

The following description will be better understood by means of the following definitions.

As used in the following and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes" and "including" are interchangeable and not intended to be limiting. It is to be further understood that where for the description of various embodiments use is made of the term "comprising", those skilled in the art will understand that in some specific instances, an embodiment can be alternatively described using language "consisting essentially of" or "consisting of."

In the frame of the present disclosure, the expression "operatively connected" and similar reflects a functional relationship between the several components of the device or a system among them, that is, the term means that the components are correlated in a way to perform a designated function. The "designated function" can change depending on the different components involved in the connection. Likewise, any two components capable of being associated can also be viewed as being "operatively couplable," to each other to achieve the desired functionality. A person skilled in the art would easily understand and figure out what are the designated functions of each and every component of the device or the system of the invention, as well as their correlations, on the basis of the present disclosure.

A "kinematic chain" is an assembly of rigid bodies or units connected by joints to provide constrained (or desired) motion that is the mathematical model for a mechanical system. The rigid bodies, or links, are constrained by their connections to other links.

A "revolute joint" (also called "hinge joint") is a one-degree-of-freedom kinematic pair used in mechanisms. Revolute joints provide single-axis rotation function used e.g. in folding mechanisms and other uni-axial rotation devices, while impeding translation or sliding linear motion.

The "degrees of freedom" or "DoF" of a mechanical system is the number of independent parameters that define its configuration. The position and orientation of a rigid body in space is defined by three components of translation (moving up and down, moving left and right, moving forward and backward) and three components of rotation (swivels left and right-yawing-, tilts forward and backward-pitching-, pivots side to side-rolling-), which means that it has six degrees of freedom. The number of degrees of freedom of a system is the number of independent variables that must be specified to define completely the condition of the system. In the case of kinematic chains, it is the number of independent pair variables needed to completely define the relative positions of all links the number of parameters needed to specify the configuration of a mechanism, in terms of the number of links and joints and the freedom of movement allowed at each joint. This number is the degree of freedom or mobility of the mechanism. Changing the values of these parameters changes the configuration of the mechanism.

For "underactuation" it is herein meant a situation by which mechanical systems cannot be commanded to follow arbitrary trajectories in configuration space. This condition can occur for a number of reasons, the simplest of which is when the system has a lower number of actuators than degrees of freedom. Accordingly, a system is herein defined as "underactuated" if it possesses more degrees of freedom than actuators.

The materials used in accordance with the present invention for the compliant layer may be soft materials such as soft polymers or structures that present mechanical compliance e.g. flexible metal sheets. In the frame of the present disclosure, a "soft" material is any material that is either compressible, reversibly compressible, elastic, stretchable or any combination thereof. The term "stretchable" is herein used to mean an intrinsic or engineered property of a material or structure that allows such material or structure to perform a large elongation upon a strain stress, typically of >5% of the elongation of a soft structure at rest, such as for instance more than about 10%, more than about 20%, more than about 50%, more than about 100% or even more than about 200% of a soft structure at rest without cracking or loss of its mechanical properties.

The term "foam" refers to a substance that is formed by encompassing a plurality of polydisperse or monodisperse gas bubbles, referred to herein as "cells", within a mass of a liquid or a solid, constituting the films of walls separating the cells. In the context of solid foams, according to some embodiments of the invention, the regions occupied by a tangible condensed mass are regarded as the "solid" fraction of the foam, while all other regions not occupied by this fraction are regarded as the "gas" fraction of the foam. According to some embodiments of the present invention, the foam is a combination of a polymeric porous solid matrix and gas-filled cells, typically filled with ambient air. A "porous solid matrix" refers to the non-gaseous part of the foam, which contributes substantially to the mass of the foam but substantially less to its volume. Porous materials in general are classified either as "open" or "closed" foams. In the terminology of foam science, closed foams have "cells" (pores, voids) where the faces shared with neighbouring "cells" are solid membranes; these closed foams entrap the pore fluid, which cannot easily escape through the solid membranes delimiting the "cells". Classical open foams have no membranes between neighbouring cells, but only struts along the edges where three or more cells meet. Such open foams naturally have a fully interconnected pore space, and a fibrous network of solid material.

The term "flexible", as used herein, designates the capacity of a component of the present device and system to actively or passively bend in one or more off-axis directions according to the actuator-driven operation and/or to the movement of a user, typically in an elastic fashion.

The term "compliant", as used herein, designates any combination of soft and flexible properties, as defined above, of an object. In particular, the term "compliant" refers to the ability of a structure or object to adapt its shape according to the shape change of a support it adheres to without substantially compromising its mechanical or functional performances. In the frame of the present disclosure, the terms "compliant" and "flexible" are used interchangeably.

As used herein, the term "orthosis" refers to static orthoses, i.e. orthoses designed to prevent or limit moveable parts. These include immobilizing orthoses, preventing any movement in the joints involved, and restrictive orthoses, which limit the movement in a specific aspect of joint range of motion. Typical static orthoses are splints, casts or braces.

The term "Activities of Daily Living" or "ADL" originates from the field of medicine and is used by physicians and occupational therapists. The expression "ADL" refers to a group of tasks and is understood as a qualitative description. Hence, vaguely defined motor performances are not described, but the general ability of successfully performing tasks are mentioned. Over time multiple sub-categories of ADL developed, for instance "Physical Self-Maintenance" (PSM) and "Instrumental Activities of Daily Living" (IADL). Such specifically defined categories of ADL are used by practicing physicians to justify medical measures. With the emergence of robotics, new sub-categories of ADL have been defined. The three major categories are: "Domestic Activities of Daily Living" (DADL), including for instance food preparation, housekeeping, laundry and telephone/computer use, "Extradomestic Activities of Daily Living" (EADL) including for instance transportation/driving and shopping, and "Physical Self-Maintenance", including feeding/medicating, toileting, bathing, dressing and grooming.

Figure 13:
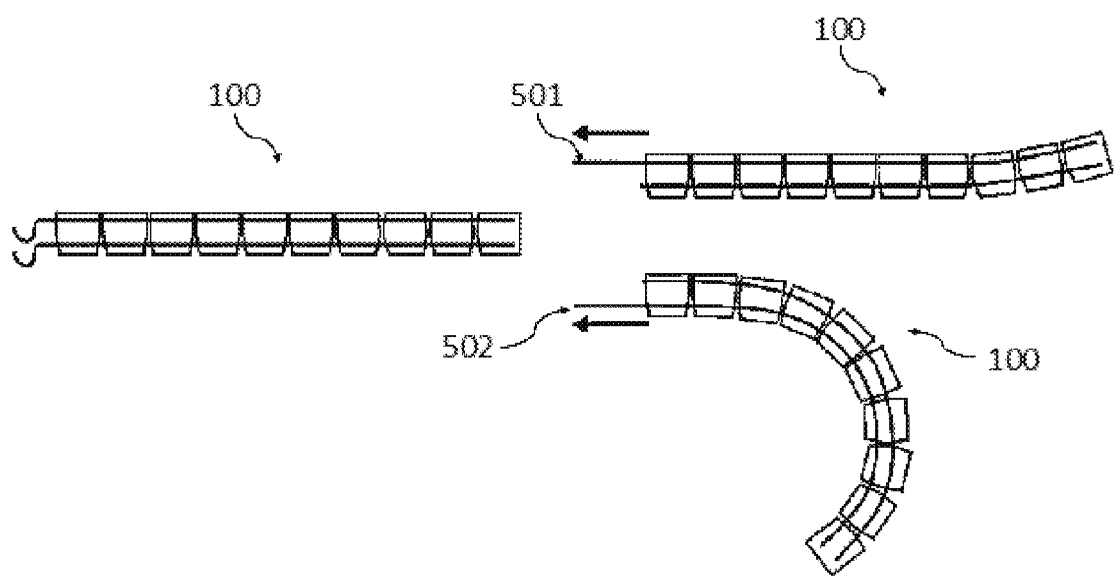
FIG. 13 depicts a model of actuation of the motion unit through flexion and tension cables.

With reference to the Figures, one exemplary, non-limiting hand exoskeleton according to a first aspect of the invention is shown, said hand exoskeleton comprising:

a) a hand- and/or wrist-wearable support 10 configured to be connected in proximity to a metacarpophalangeal (MCP) joint of a user; and b) an elongated motion unit 100 operatively connected to, or stemming from, the hand- and/or wrist-wearable support 10, said motion unit comprising:

i) a plurality of adjacent movable members 1000 located along the longitudinal axis of the motion unit 100, each movable member 1000 comprising a first and second cavity 301 and 302 along its entire length;

ii) a compliant layer 400 running through said motion unit 100 and along the longitudinal axis of the motion unit 100;

iii) a first cable or wire 501 running inside said first cavity 301 and connected to the motion unit 100;

iv) a second cable or wire 502 running inside said second cavity 302 and connected to the motion unit 100; and v) at least one finger support or one finger support 600 configured to locate two fingers of a user wearing the exoskeleton wherein said motion unit 100 is connected at one end to the finger support 600. When pulled, cable or wire 502 allows for flexion of the motion unit 100, whereas pulling of cable or wire 501 allows for extension of the motion unit 100, thereby flexing or extending fingers of a user wearing the device (see FIG. 13).

The motion unit 100 comprises a plurality of adjacent movable members 1000 located along the longitudinal axis of the motion unit. Each pair of adjacent movable members 1000 represent a kinematic pair mechanically coupled through 1 DoF revolute joint, and the entirety of the movable members 1000 defines a kinematic chain having "n" DoFs, wherein "n" is equal to the kinematic pairs of the kinematic chain. Typically, "n" can be comprised between 2 and 50 (FIGS. 8-11). The 1 DoF revolute joint is guaranteed by the physical contact between adjacent movable members 1000, kept together in place by the presence of the compliant layer 400, typically running in embodiments of the invention through a third cavity located between first and second cavity 301 and 302.

Particularly, according to one embodiment, said motion unit 100 comprises:

i) a first, top layer 101 of partial movable members 201 comprising a first cavity 301 along its entire length;

ii) a second, bottom layer 102 of partial movable members 202 comprising a second cavity 302 along its entire length;

iii) a compliant layer 400 located between said first, top layer 101 and said second, bottom layer 102;

iv) a first cable or wire 501 running inside said first cavity 301 and connected to said first, top layer 101;

v) a second cable or wire 502 running inside said second cavity 302 and connected to said second, bottom layer 102; wherein each partial movable member of said top layer faces a partial movable member of said bottom layer to define a complete movable member 1000; and c) at least one finger support 600 configured to locate two fingers of a user wearing the exoskeleton, wherein said first and/or second layer 101/102 of motion elements is/are connected at one end to the finger support 600. The advantage of this embodiment of the invention relies mainly in its modularity and the possibility of locally tailoring the operation/action of motion elements 1000 by working on the positioning and shape of the partial motion elements and the compliant layer 400.

Figure 4:
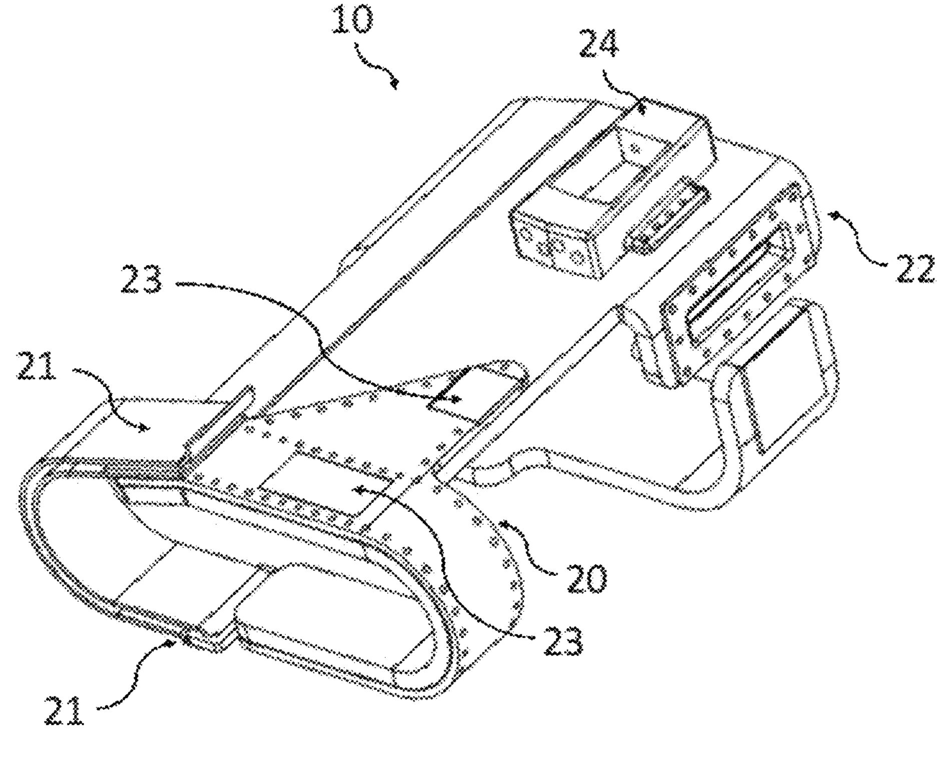
FIG. 4 depicts an isometric view of one embodiment of the hand- and/or wrist-wearable support according to the invention.
Figure 5:
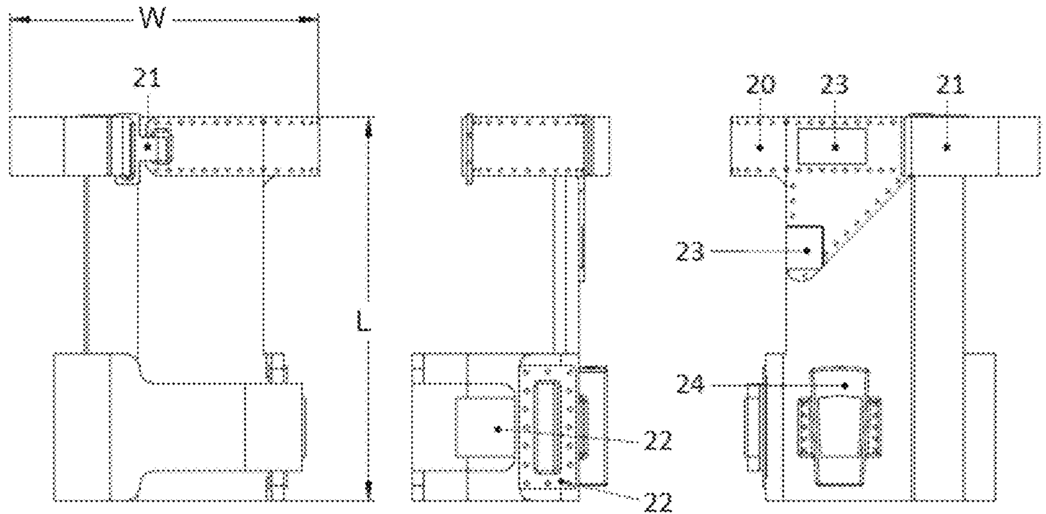
FIG. 5 depicts lateral and top views of the same embodiment of FIG. 4 of the hand- and/or wrist-wearable support.

One non limiting embodiment of the wearable support 10 is depicted in FIGS. 4 and 5. The shown wearable support 10 is composed of a partial glove with an integrated rigid U-shaped bracket 20 located on or in proximity to a metacarpophalangeal (MCP) joint of a user once worn (i.e., just close or in contact to the knuckles of a wearer), and provides a stable anchor point. Adjustable means for fixation 21 comprise a rubber band with a small hook used to close the loop of the U-shaped bracket 20 after donning the exoskeleton. The partial glove only covers the dorsal side of the hand. A cuff 22 can be integrated into the glove to provide a stabilisation of the wrist. Adjustable hooks-and-loops rings or soft elastic threads can be used alternatively or additionally for fixing the wearable support 10 on the hand of the user. One main advantage of said configuration relies in the freedom of the fingertips of a user from any external structure such as gloves, thimbles or haptic/position sensors, so to facilitate wearing and keep unaltered the somatosensorial perceptions of the user. As it will be evident, the artificial tendons are conveniently worn by users on the back of their hands, so to leave both the palm and the fingertips unfettered. On the dorsal side of the glove a splitter 24 can be integrated to allow the actuation of multiple fingers and to act as a strain reliever for the inertia of the actuation.

Figure 14:
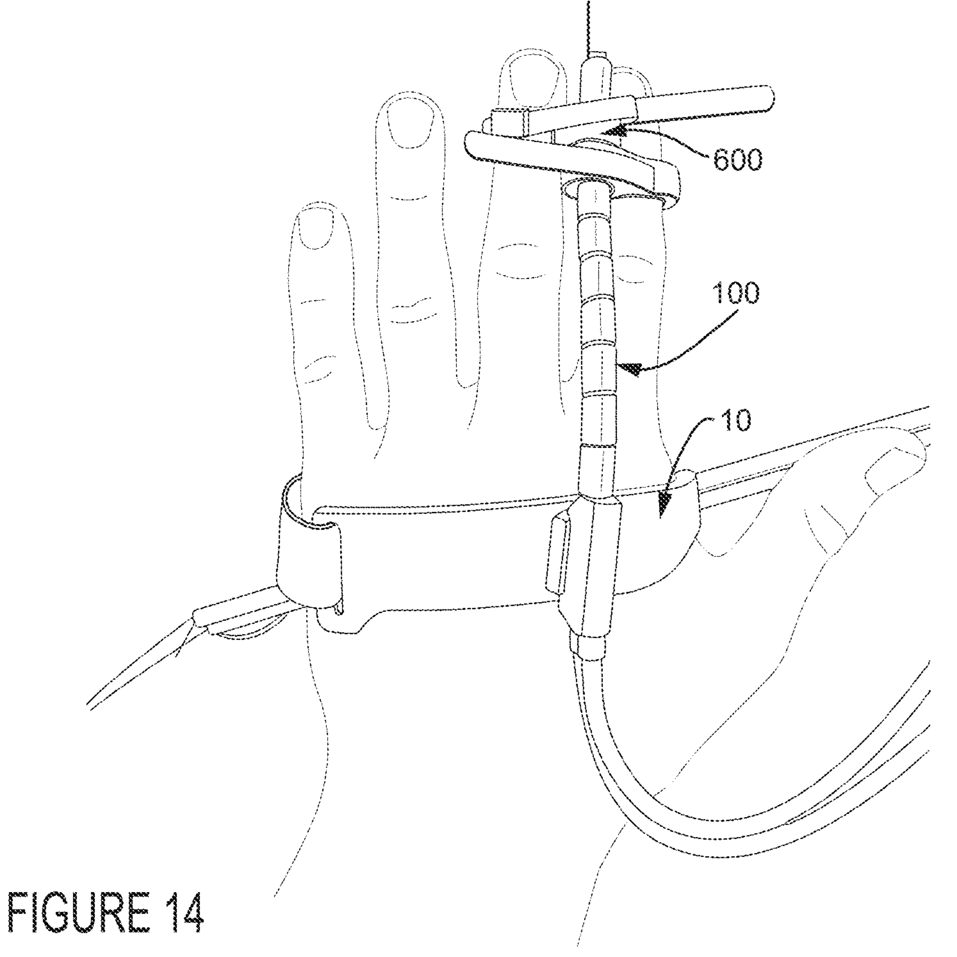
FIG. 14 shows another implemented embodiment of the system of the invention worn by a user.

In another scenario, the wearable support 10 is embodied as a splint or similar orthoses configured to sit behind the MCP joints of a user and to fixate the mechanism to the user's hand through connection means in the form of rails 23 in a way to allow comfortable closing of the hand. Rails 23 consent to easily connect and disconnect the motion unit 100 mechanism to the splint 10, for example to wash the splint 10 or separate the motion unit 100 for maintenance. Rails 23 are located onto the hand wearable support 10 in a position that allows a connected motion unit 100 to run parallel and between two fingers of a user when worn (see for instance FIG. 14).

Figure 12:
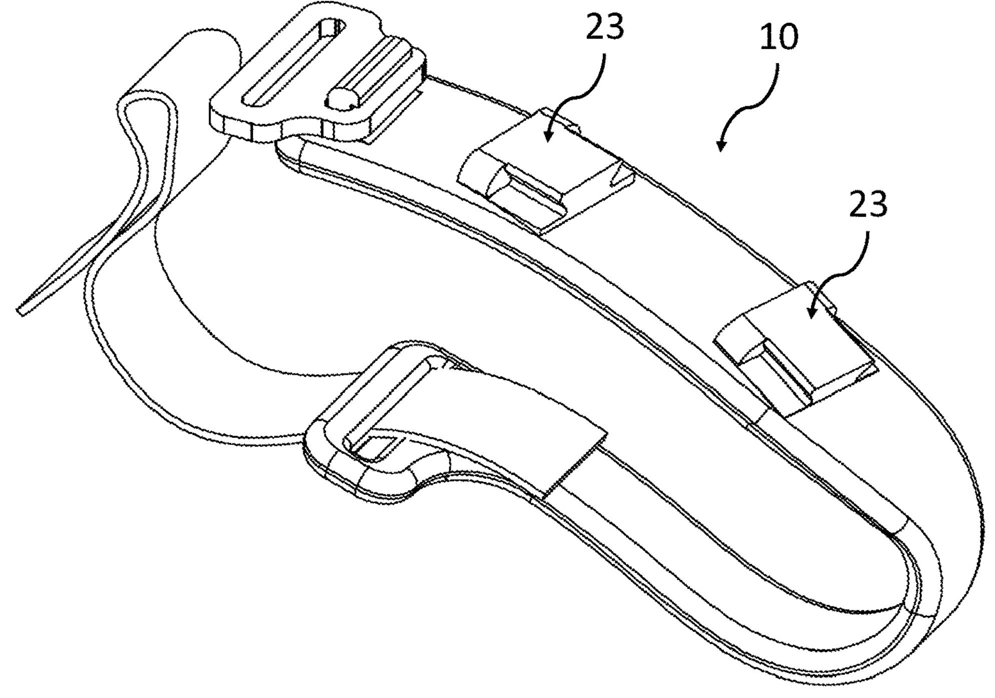
FIG. 12 depicts an isometric view of another embodiment of the hand- and/or wrist-wearable support according to the invention. The support is embodied as a splint orthosis.

The proximal transverse palm crease (proximal line on the palm, which starts at crotch) can be considered the position of the centre of rotations of the MCP joints. In order to fit users with different hand circumferences, the splint 10 may be designed with inherent flexibility, and can be entirely closed in a cuff-like configuration or may comprise adjustment means/closing means such as hooks and loops, buttons, magnetic buttons or belts. To achieve autonomous usage of the device specifically for stroke patients, users must be able to don and doff the splint using only one hand. As shown in FIG. 12, the splint 10 is open on one side and can be pushed on the hand from one side. It has the additional advantage to be easily usable by stroke patients, who have contracted closed fingers. Finally, to increase comfort and breathability, the splint 10 may be padded with soft materials such as e.g. a neoprene (for instance sewed using small integrated holes) or a soft silicone (overmolded during the manufacturing).

Turning now to the elongated motion unit 100, this is operatively connected to, or stemming from, the hand- or wrist-wearable support 10. In one embodiment, the elongated motion unit 100 stems from the support 10, and represents therefore a built-in, elongated portion of this latter. Motion unit 100 can for instance comprise a proximal portion integrated into the support 10 by means of additive manufacturing processes, such as 3D printing or the like. Alternatively, and preferably, the elongated motion unit 100 is coupled to the support 10 through methods known in the art, such as plug-and-socket means, welding, soldering, brazing, adhesive, magnetic means etc. In one embodiment, the elongated motion unit 100 is coupled to a U-shaped bracket 20 via connection means such as multiple magnets 23 located on a proximal connector plate 103. In the case of an overload, the magnets are able to disengage and prevent harm for the wearer (see for instance FIGS. 1, 6 and 7). The elongated motion unit 100 is coupled to the support 10 through connection means 23 so that the proximal end of the elongated motion unit 100 is located between two fingers of a user when worn, such as between an index and a middle finger in FIGS. 1, 6, 7 and 14.

Figure 2:
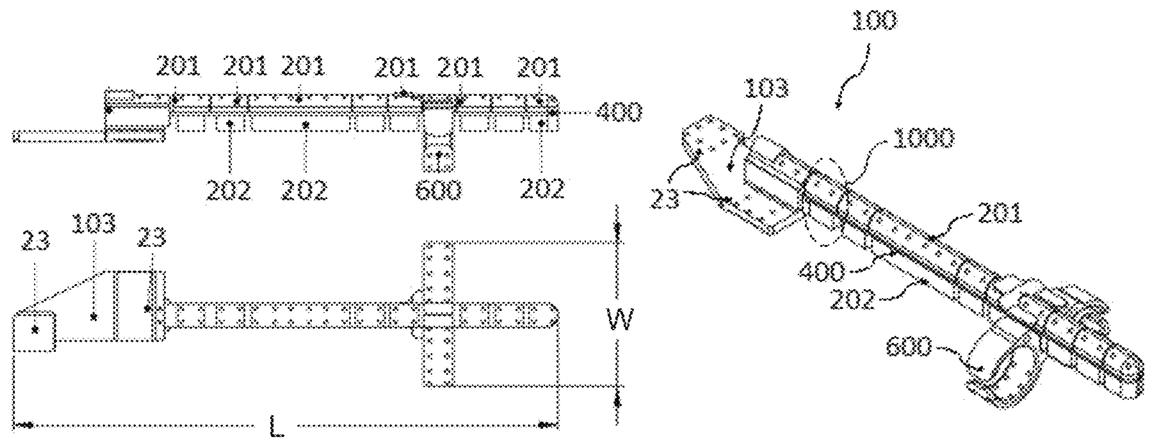
FIG. 2 depicts a lateral view, top view and isometric view of one embodiment of the elongated motion unit of the invention. The embodiment shows a top layer and a bottom layer of movable members sandwiching a compliant layer in between. One of the movable members is different in size and shape compared to the others.
Figure 3:
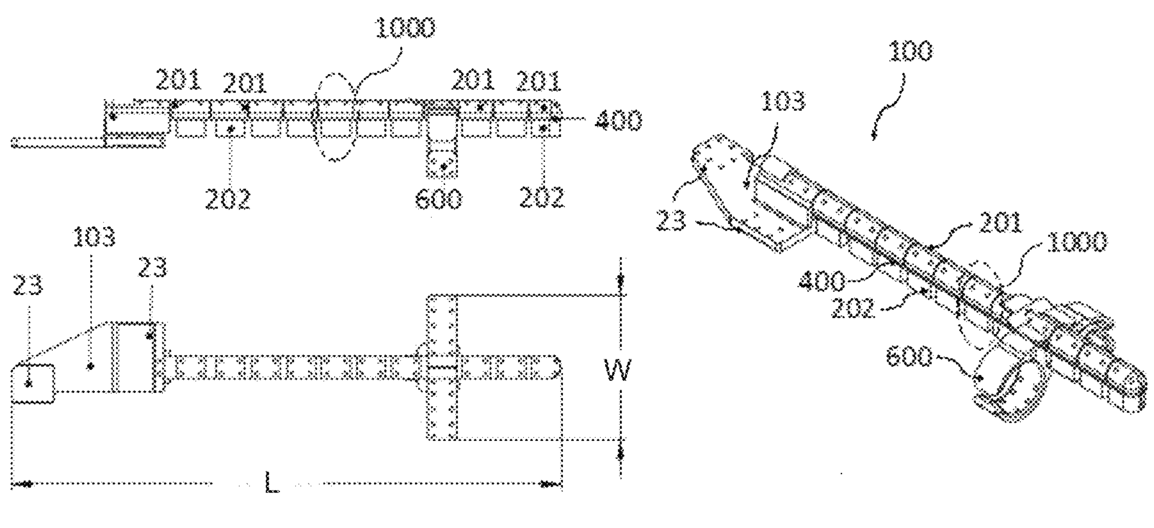
FIG. 3 depicts a lateral view, top view and isometric view of one embodiment of the elongated motion unit of the invention. The embodiment shows a top layer and a bottom layer of movable members sandwiching a compliant layer in between. All the movable members have the same size and shape.
Figure 6:
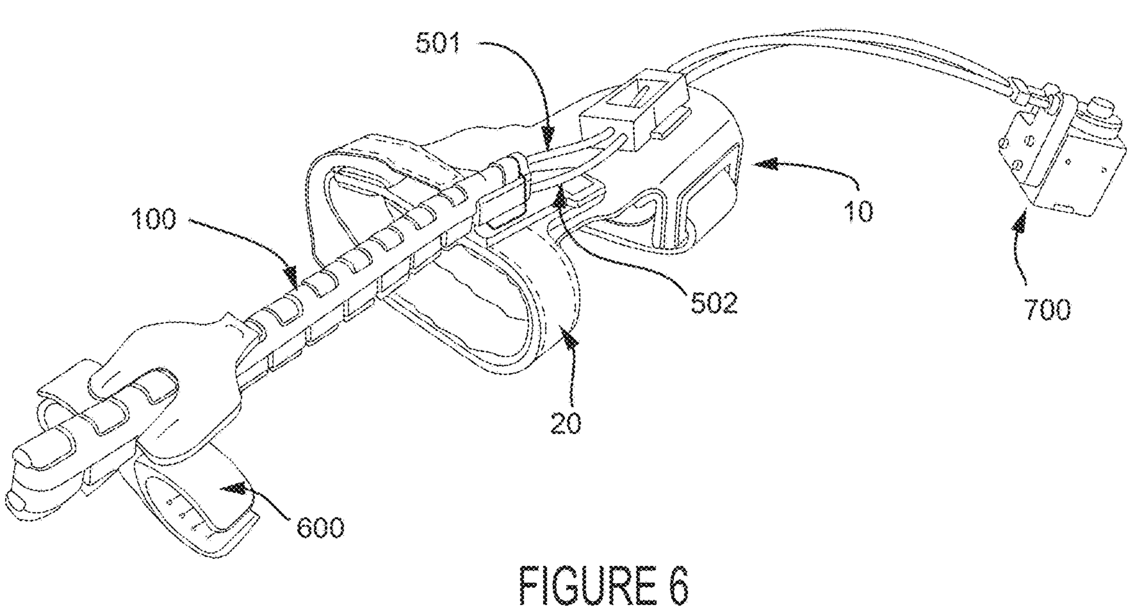
FIG. 6 shows an implemented embodiment of the system of the invention.
Figure 7:
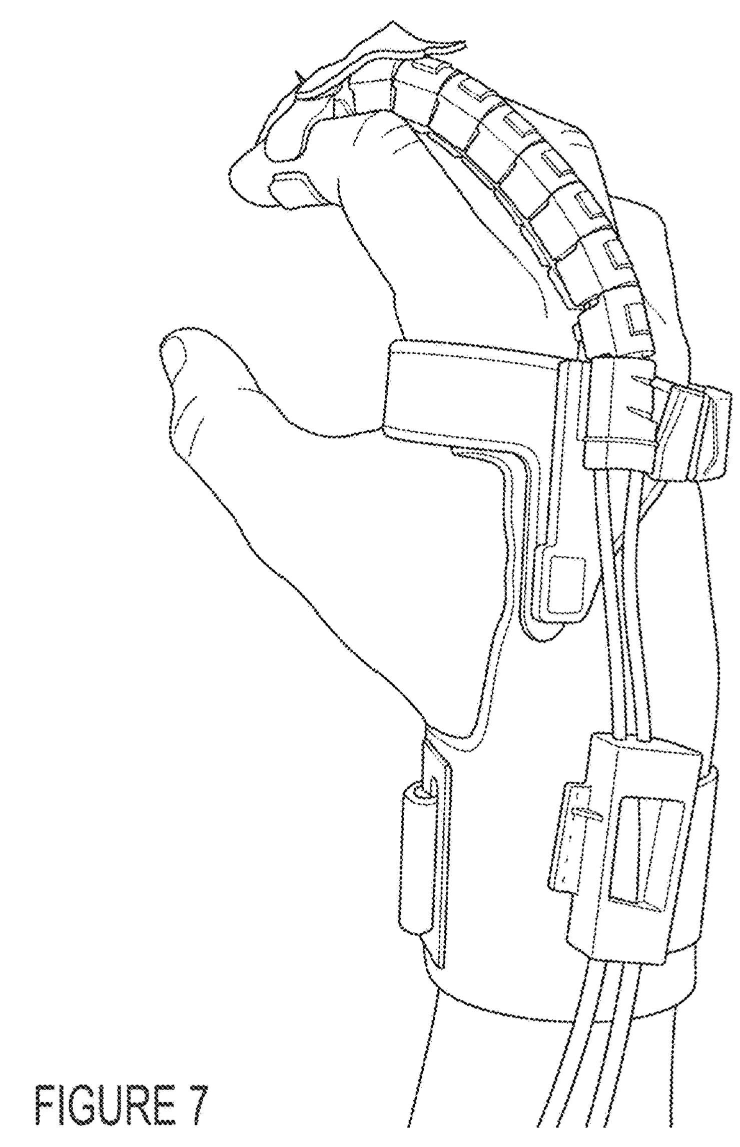
FIG. 7 shows the same system of FIG. 6 worn by a user.
Figure 8:
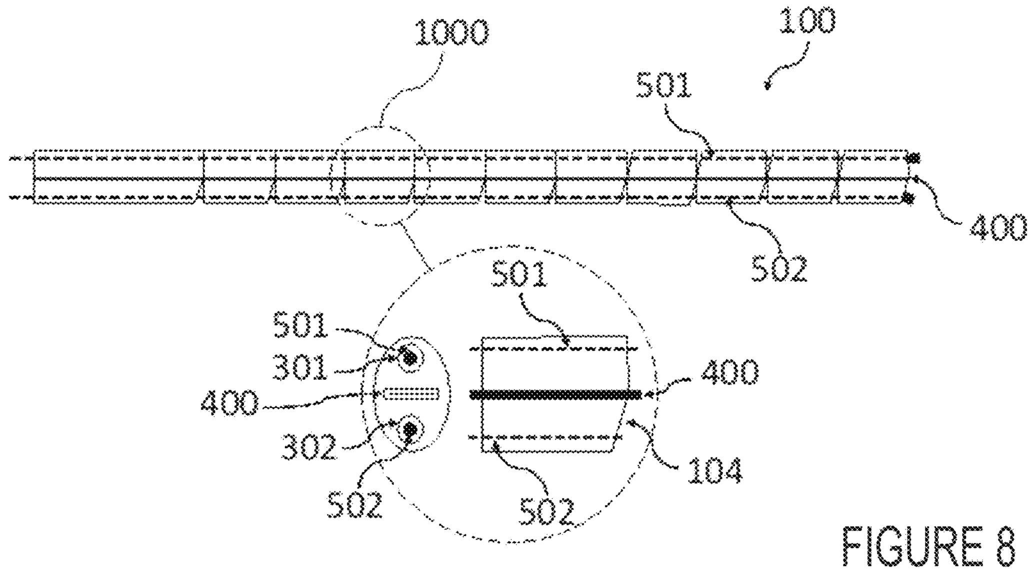
FIG. 8 depicts a lateral cross-section of one embodiment of the elongated motion unit according to the invention. The movable members are independent physical units mechanically connected between them through the compliant element running therethrough. The movable elements have different shapes and cutouts characteristics.
Figure 9:
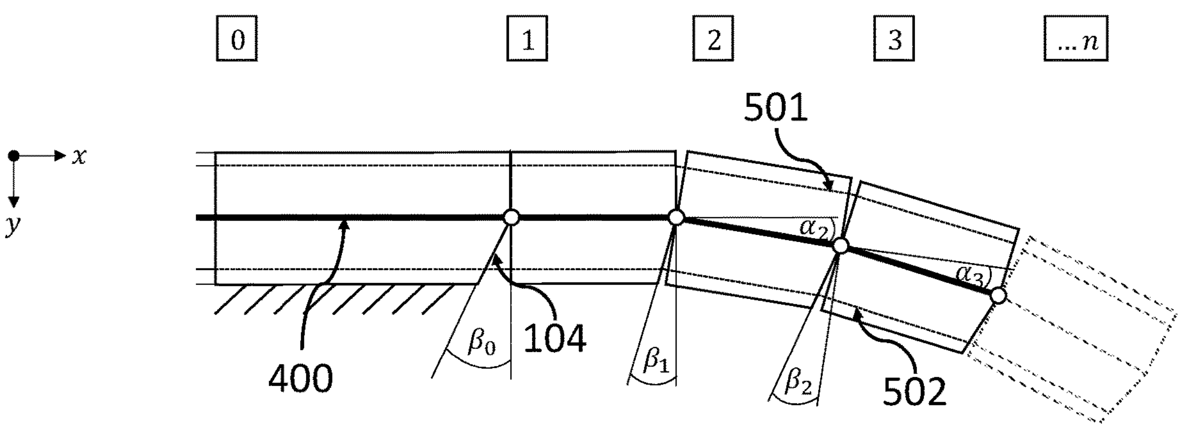
FIG. 9 depicts a two-dimensional model of the motion unit movement with one-dimensional rotational joints between adjacent movable members. The elongated motion unit is embodied as the one shown in FIG. 8.
Figure 10:
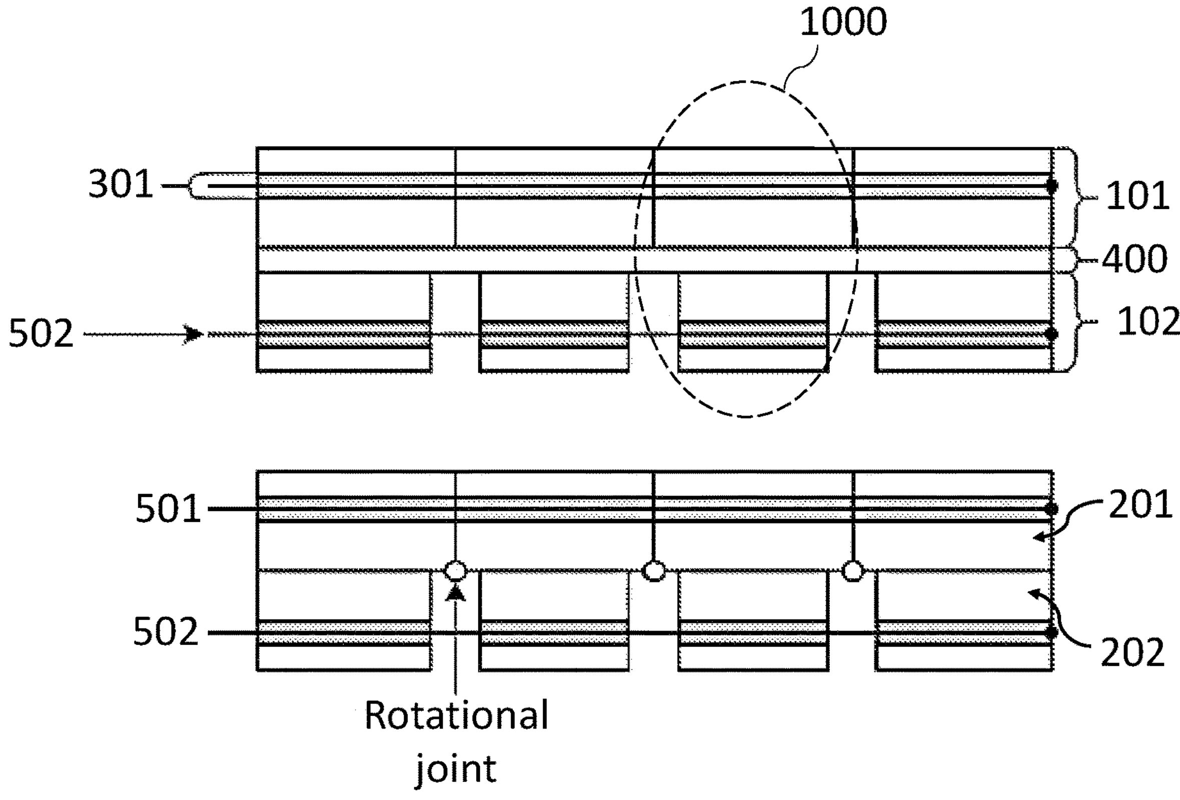
FIG. 10 depicts a mechanical equivalent model of the elongated motion unit shown in FIG. 3.

In one embodiment, the design of the motion unit 100 is based on a continuous three layer "sandwich" structure, in which two "hard" layers are separated by a "soft backbone" layer (see FIGS. 2, 3 and 6). A first, top layer 101 comprises a plurality of rigid or semi-rigid, such as plastic or silicon-based, partial movable members 201, and a first cavity 301 running along its entire length. The second, bottom layer 102, comprising a second cavity 302 along its entire length, is mirroring the top layer 101. The first and second cavities 301/302 each accommodate a cable or wire 501/502 running inside said cavities, and connected to said first, top layer 101 and second, bottom layer 102, respectively, typically at the distal tips of said layers 101/102. Cables or wires 501/502 can be attached on the distal end tip of their respective layers by any suitable attachment technique such as welding, soldering, brazing, adhesive and the like. First and second cable or wire 501/502 can be polymeric cables, metallic cables, fabric cables or any other suitable cable or wire structure able to transmit a tension and/or pulling forces from an actuator to the motion unit 100. In one embodiment, the first and/or second cable or wire 501/502 is/are constituted by a Bowden cable, a type of flexible yet uncompressible cable used to transmit mechanical force or energy by the movement of an inner cable relative to a hollow outer cable housing. A Bowden cable typically comprises an optional plastic coating or sheath, a steel structure, an optional inner sleeve to reduce friction and an inner cable. Bowden cables are widely accessible and low cost, thus reducing the manufacturing-associated price. Of course, other equivalent systems may be used within the scope of the present invention.

Cables or wires 501/502 are configured to be connected on a distal end to the motion unit 100, particularly to the distal tip thereof, and on an opposite proximal end to bi-directional actuating mechanism or unit 700, as will be described herein below. At the same time, cables or wires 501/502 and cavities 301/302 are also configured the ones with respect to the others in such a way that each cable can slide along the respective cavity upon actuation of the unit 700, thereby permitting the bending or straightening motion of the motion unit 100 depending on the needs. Accordingly, the diameter or otherwise cross-section of the cavities 301/302 are larger than the diameter/cross-section of the cables 501/502. For instance, the cables may have a diameter of 0.8 mm and the cavities a diameter of 1.5 mm.

The flexible backbone located in between the two layers 101/102 is represented by a compliant element 400. Element 400 is composed in some embodiments of soft polymers having an elastic modulus comprised between about 1 MPa and about 1 GPa. Exemplary soft polymeric material can be selected from a non-limiting list comprising thermosets or thermoplastics such as styrene butadiene styrene (SBS) or styrene ethylene butylene styrene (SEBS), Nylon, Polyether block amide (PeBax) polyamide, Polyvinyl alcohol (PVA), polyimide (PI), poly ethylene (PE), poly propylene (PP), polyether etherketone (PEEK), Acrylonitrile butadiene styrene (ABS), epoxys, polytetrafluoroethylene (PTFE); soft foams such as polyurethanes (PU) including reticulated polyurethanes; flexible polyvinyl chloride (PVC), neoprene, uncrosslinked neoprene, cross-linked polyethylene (PE), polyethylene terephthalate (PET) polyether, ethylene-vinyl acetate (EVA), polyethylene-vinyl acetate (PEVA), polypropylene glycol (PPG), latex; elastomeric materials such as silicone rubber (e.g. polydimethylsiloxane PDMS) or fluorosilicone rubber; thermoplastic elastomers such as styrenic block copolymer (SBC), ethylene propylene diene monomer (EDPM) rubber, butyl rubber, nitrile rubber or any combination of the foregoing. Preferably, the compliant element 400 comprises a stretchable polymeric material. In additional or alternative embodiments, the compliant element 400 may comprise a flexible element such as a metal sheet. In the present embodiment, the compliant element 400 is sandwiched between first and second layers 101/102.

In one embodiment, the compliant element 400 has a variable thickness, shape and/or composition along one or more portions of its length. In this configuration, the element 400 structure and function can be tailored depending on the needs and circumstances to precisely defined the motion of the motion unit 100, and adapt the exerted forces on specific portion of the motion unit, by locally altering its mechanical properties. This design may allow to better conform to the anatomy of a user's finger, and at the same time it may facilitate and focus a discharge or an elongation pressure only where it is needed. For instance, the compliant element 400 can vary in thickness in correspondence of one or more finger joints of the user wearing the exoskeleton, in correspondence of one or more partial movable members 201/202 of top and/or bottom layer 101/102, and/or in correspondence of joints between one or more partial movable members 201/202. This configuration may help for instance the optimization of the bending forces at specific locations along the motion unit 100. In an alternative or additional scenario, some rigid plastics, textiles or any other suitable material/component having a different (higher or lower) elastic modulus with respect to the main material composing the compliant element 400 can be added or embedded during the manufacturing process or thereafter into or onto said element 400. For instance, reinforcing fibers or metal particles can be embedded into a soft polymeric material forming the compliant element 400, in one or more portions, so to locally form composite materials having different mechanical properties compared to the bare, starting material.

In the present embodiment, one important aspect relates to the design of the first and second layers 101/102, as well as of the partial movable members 201/202 thereof. These partial movable members 201/202 can vary in size (length, thickness, width), shape and/or material, within the same layer or between different layers. Preferably, partial movable members 201/202 can vary in size (length, thickness, width), shape and/or material within the same layer (that is, elements of the same layer can have different size, shape and/or material). The partial movable members 201/202 can be composed of rigid, hard materials such as hard plastics or composites thereof, and can be segments of a single body layer or independent units mechanically interconnected between them. The portions all together form a layer.

For the sake of clarity, for "rigid motion elements" is herein meant those portions of a layer that do not conform to a substrate they adhere to, or that they do not adapt so to change their shape according to the shape change of the support they adhere to (i.e. they are not compliant and not deformable upon application of a bending force). A "rigid" or "non-deformable" object is capable to distribute a load and resist deformation or deflection upon contact with a target item, in an operational bending setting. Typical materials used in this context can include without limitations rigid or semi-rigid plastics such as Polyethylene (PE), Polyvinyl Chloride (PVC), Polypropylene (PP), Polylactic Acid (PLA), Polycarbonate (PC), Polymethylmethacrylate (PMMA), Polyoxymethylene (POM), ABS (Acrylonitrile Butadiene Styrene) and the like; metals (including alloys thereof), ceramics, wood and glass. "Rigid" or "non-deformable" materials according to the invention are characterized by a sufficiently high stiffness, described by their flexural strength (stress at failure in bending in a flexure test), allowing a deformation or deflection of a motion element of no more than 5% in terms of bending.

The expression "flexural strength" refers to a material property defined as the stress in a material just before it yields in a flexure test. The transverse bending test is most frequently employed, in which a specimen having either a circular or rectangular cross-section is bent until fracture or yielding using the well-known three or four point flexural test technique, according for instance to ASTM D790 and ISO 178 standards of measurement. The flexural strength represents the highest stress experienced within the material at its moment of yield.

Accordingly, non-deformable materials used according to the invention have a stiffness in terms of flexural strength typically comprised between 10 MPa and 1 GPa, and a flexural modulus typically comprised between 1 and 20 GPa.

Advantageously, in one embodiment, said first, top layer 101 and/or said second, bottom layer 102 of partial movable members is (are) configured as (a) monolithic structure(s). In another embodiment, said first, top layer 101 and/or said second, bottom layer 102 of partial movable members is composed of a plurality of mechanically interconnected, independent units, such as rigid units. Importantly, in all embodiments, each partial movable member 201 in the first layer 101 is facing a partial movable member 202 in the second layer 102 so to define a complete movable member 1000, further comprising a portion of the compliant element 400 located/sandwiched in between.

Figures 15, 16:
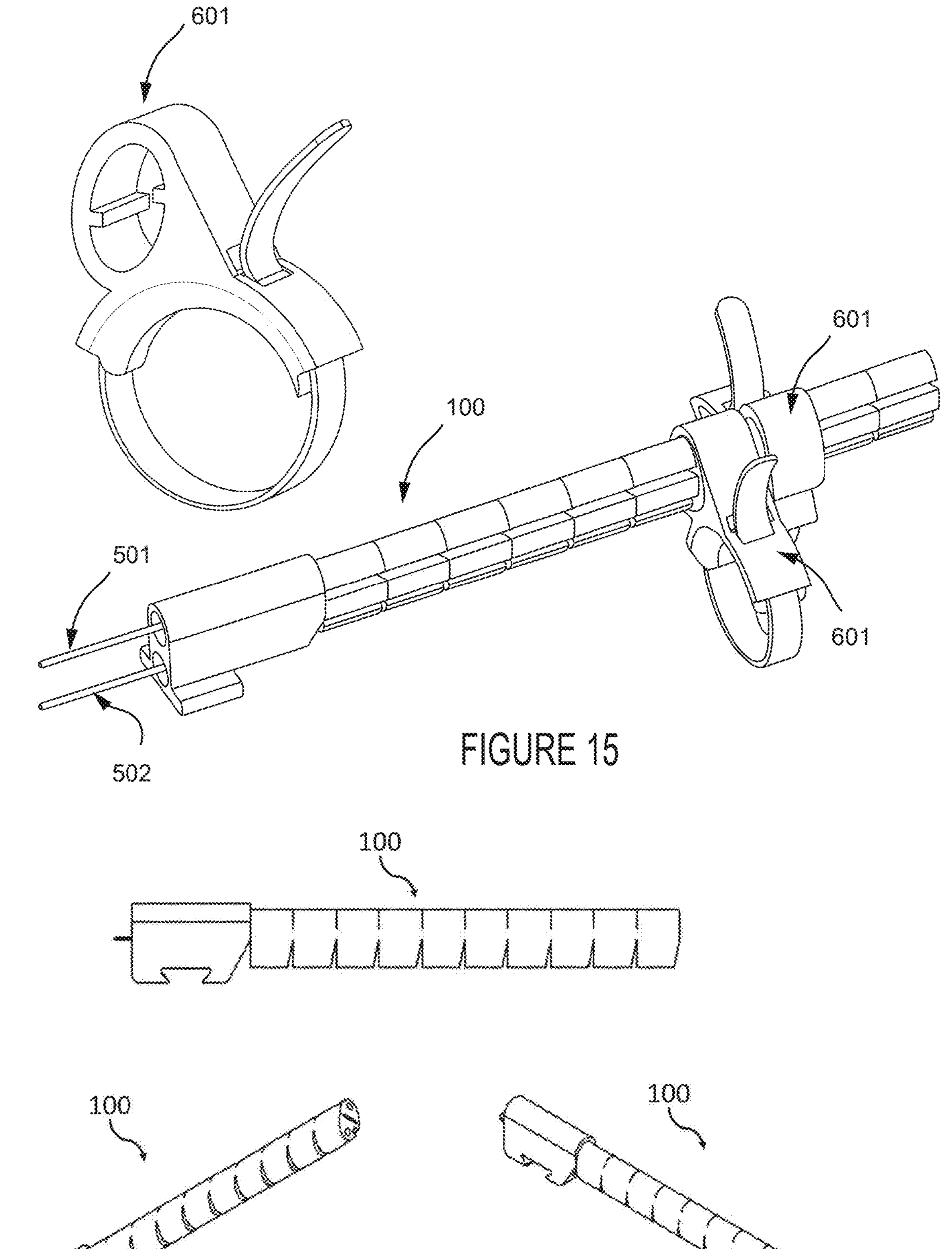
FIG. 15 depicts a finger support according to the invention composed of two partial finger supports, each configured and located along the motion unit to accommodate one finger of a user. In the shown embodiment, each partial finger support include means for adjusting the size thereof.
FIG. 16 depicts one lateral and two isometric views of one embodiment of the motion unit according to the invention, wherein the entire motion unit is embodied as a monolithic structure.

In other embodiments, the entire motion unit 100 is composed of a monolithic structure. No bottom and top layers 101/102 are present, rather each movable member 1000 is composed of a single-block unit comprising cutouts 104 (see FIGS. 8 and 16). Every movable member 1000 is physically and mechanically connected to the adjacent one (s) through a connection point, that acts also as a rotational joint between adjacent movable members 1000, in a monolithic motion unit 100 (see FIGS. 8 and 16). This embodiment is advantageously obtainable via additive manufacturing procedures well known in the art such as 3D printing and the like or through standard techniques such as injection molding. In this embodiment, as well as in embodiments where no first and second layers 101/102 are present, the compliant element 400 (such as a metal sheet) typically runs through the adjacent movable members 1000 and along the longitudinal of the motion unit 100 inside a cavity.

In embodiments of the invention, the complete or partial movable members have different sizes and/or composition one compared to another. Particularly, the complete or partial movable members may have different length (L), width, thickness and/or shape one compared to another. In embodiments of the invention, the complete or partial movable members have different lengths (L) one compared to another. In embodiments of the invention, the complete or partial movable members have different shapes one compared to another. In embodiments of the invention, the complete or partial movable members of a same layer have different length (L), width (W), thickness and/or shape, particularly lengths and/or shape, one compared to another. The complete or partial movable members can have for instance any lateral cross-section (perpendicular to the longitudinal axis) such as round, elliptic, square, rectangular and the like. Tailoring the size and/or composition of the complete or partial movable members, even individually, is useful to precisely distribute the flexing/extending force upon actuation of the exoskeleton to optimally adapt grasping to users with different morphologies or to locally alter the kinematics of the actuated structure, enabling e.g. to locally increase or decrease the bending radius across its longitudinal axis.

A particular aspect of the invention relates to the design of the movable members 1000 of the motion unit 100. Advantageously, said movable members 1000 comprise cutouts 104 on at least a surface thereof, said cutouts being configured to permit the bending of the motion unit 100 in a bending direction of a user's finger. In embodiments of the invention, said cutouts 104 have different size features, including lengths and/or angles, from one movable member 1000 to another (FIGS. 2, 3 and 8-11). In the appropriate embodiments, at least the partial movable members 202 of the second layer 102 comprise cutouts 104 on at least a surface thereof. Cutouts as described herein provide space for the motion unit 100 to curl, and represent an advantageous technical feature for what concerns the possibility of rationally engineering the flexibility of the motion unit 100 by readily accessible manufacturing method(s). Accordingly, the motion unit 100 is rendered single-sided deflectable by cutting slots or gaps 104, passing partially or completely through the entire thickness of the second layer 102, so that a sort of "spine with ribs" is formed. In other embodiments, also the first layer 101 may comprise cutouts 104. For the sake of clarity, cutouts according to the invention can be embodied as portions of a layer that have been removed so to reduce the size of a motion element, or as portions of a layer that have been removed so to change the shape of a motion element, as in the case of a triangular cutout, defining a bending angle typically comprised between 0 and 160°.

Another important aspect of the invention relates to the finger support 600. This is configured to locate two fingers of a user wearing the exoskeleton, and is preferably located on a distal portion of the elongated motion unit 100, and in proximity to the distal phalanges of a user wearing the exoskeleton. One interesting aspect of this configuration relies in the way the exoskeleton is intended to be used: in fact, to optimize the forces exerted on the user's fingers, the motion unit 100 is configured to be placed between the two fingers of a user located into the finger support 600. This can be embodied for instance as a double ring to accommodate two fingers at once, and can slide on the outside of the motion unit 100 to compensate for required changes in length during the curling process. Alternatively, finger support 600 can be embodied as a single cuff designed to accommodate two fingers in the same cavity, or may be composed of two partial finger supports 600', each configured and located along the motion unit 100 to accommodate one finger of a user (see FIGS. 14 and 15). Finger support 600 or partial finger supports 600' may include means for adjusting the size thereof, in order to adapt the loading cavity to any finger's circumference. Advantageously, compared to hand exoskeletons known in the art, the positioning of the motion unit 100 between two fingers greatly adds torsional stiffness to the elongated motion unit without complicating the design of the entire device (FIGS. 1-3, 6-7 and 14).

As it will be apparent, another aspect of the present invention relates to a hand exoskeleton system comprising the hand exoskeleton as described herein operatively connected to a bi-directional actuating mechanism (FIGS. 1 and 6). The bi-directional actuating mechanism is operatively connected to the first and second cables or wires 501/502 and may be a conventional actuator 700 that implements a linear motion to pull the cables or wires 501/502 along their longitudinal axes. As a way of non-limiting example, the actuator 700 may be embodied as a pneumatic or hydraulic piston engine comprising a piston contained by a cylinder; alternatively, the actuator 700 may be embodied as a commercially available rotational actuator having a moving organ operatively connected with the cable wires 501/502; still alternatively, the actuator 700 may be a rotational actuator coupled to a spool to turn in a way to wind up/unwind the cables or wires 501/502. In one embodiment, actuator 700 may be a linear servomotor, using a closed-loop, error-sensing approach for position feedback to control/correct its motion and final position of the cable wires 501/502. The entire actuating mechanism may be power-supplied by an external energy source or embedded batteries, and may further comprise means for wired or wireless connection of the entire system to external devices such as computers, tablets, smartphones, microcontrollers and the like.

The entire system may comprise a data processing apparatus 800 operatively connected with the system, the data processing apparatus having a processor comprising instructions configured to operate the system to perform control of a user's fingers flexion and extension. The data processing apparatus 800 of the invention can comprise any suitable device such as microcontrollers, computers, smartphones, tablets, voice-activated devices (i.e. smart speakers/voice assistants) and the like.

In one embodiment, the data processing apparatus 800 comprises memory storing software modules that provide functionality when executed by the processor. The modules include an operating system that provides operating system functionality for the apparatus. The system, in embodiments that transmit and/or receive data from remote sources, may further include a communication device, such as a network interface card, to provide mobile wireless communication, such as Bluetooth, infrared, radio, Wi-Fi, cellular network, or other next-generation wireless-data network communication. In other embodiments, communication device provides a wired network connection, such as an Ethernet connection or a modem.

Particularly, in one embodiment the system further comprises an operatively connected data processing apparatus 800 having a processor comprising instructions configured to operate at least one of i) a power supply operatively connected with the system, ii) the bi-directional actuating mechanism 700 and iii) optional sensors 900.

As anticipated, in some embodiments the system further comprises one or more sensors 900 operatively connected with the data processing apparatus 800 and with other portions of the system such as the hand- and/or wrist-wearable support 10, the finger support 600 and/or the motion unit 100, the sensors 900 being configured for instance to measure, detect and/or analyse a parameter of the system and/or of the surrounding environment.

A "sensor" as used herein is a device that detects (and possibly responds to) signals, stimuli or changes in quantitative and/or qualitative features of a given system, or the environment in general, and provides a corresponding output. The output is generally a signal that is converted to human-readable display at the sensor location or transmitted electronically over a network for reading or further processing. The specific input could be for instance light, heat, motion, moisture, pressure, or any one of a great number of other environmental phenomena. According to the invention, a sensor 900 preferably comprises means for detecting and possibly storing a system's parameter, an environmental parameter or a combination thereof. The sensor 900 can therefore comprise a data storage device to hold information, process information, or both. Common used data storage devices include memory cards, disk drives, ROM cartridges, volatile and non-volatile RAMs, optical discs, hard disk drives, flash memories and the like. A sensor 900 according to the present disclosure may be for instance a position sensor, an optical sensor such as a light sensor, infrared sensor or a camera, a motion sensor, a velocity sensor, a touch sensor, a proximity sensor, a temperature sensor, a microphone, a force/torque sensor, as well as combinations thereof.

Sensors 900 may further comprise means for transmitting the detected and possibly stored data concerning the above-mentioned parameters to the data processing apparatus 800, in some embodiments through a wireless connection. "Wireless" refers herein to the transfer of information signals between two or more devices that are not connected by an electrical conductor, that is, without using wires. Some common means of wirelessly transferring signals includes, without limitations, WiFi, bluetooth, magnetic, radio, telemetric, infrared, optical, ultrasonic connection and the like. In one embodiment, sensors 900 further comprise means for wirelessly receiving a feedback input from a computer able to regulate the functioning of the system.

Notwithstanding the usefulness of the device of the invention in hand rehabilitative and assistive contexts, it may be as well used in different settings such as virtual or augmented reality, for gaming, telemanipulation or in mixed situations in which e.g. virtual reality is exploited for rehabilitation purposes.

EXAMPLES

The device and system of this invention has the objective to enhance the quality of life of people experiencing hand motor impairments e.g. after a stroke, for addressing issues related to rehabilitation and assistance. Aiming at the development of a hybrid device with a dual intended use can bring multiple benefits to the user. The repetitive movement therapy with the device can easily combined with functional tasks in daily living. Moreover, users are able to continue their movement therapy autonomously at home and thereby it can enable higher intensity of the training and relieve burden from therapists.

For movement therapy as well as for assistive purposes, the device allows to fully flex and extend two or four fingers of the impaired hand while realizing a natural movement, as well as sufficient closing to perform tasks of ADL. The system allows to reach a minimum total grip force of 10N for successful and safe manipulation of objects up to a weight of 1.5 kg.

The actuation unit is lightweight and compact to ensure mobility and portability, with the actuator and battery not heavier than 3 kg.

Detailed Design

Analytical Quasi Static Model of the Mechanism

The center piece of the hand exoskeleton is the mechanism which curls and straightens the wearer's fingers. In order to develop the best possible design a detailed understanding of such mechanism is required. Hence, an analytical model of the mechanism is developed.

Mechanical Equivalent

The sandwich structure of the mechanism utilizes a compliant backbone layer to allow one dimensional bending. The sandwich structure is manufactured to inherit one degree of freedom, rotation, between the rigid elements. In the mechanical equivalent model, the soft backbone structure is replaced with rotational joints at the corresponding positions. FIG. 30(*b*) shows the two dimensional model of the mechanical equivalent mechanism. A two dimensional representation is used due to the constant cross section of the mechanism.

Analytical Quasi Static Model

Figure 11:
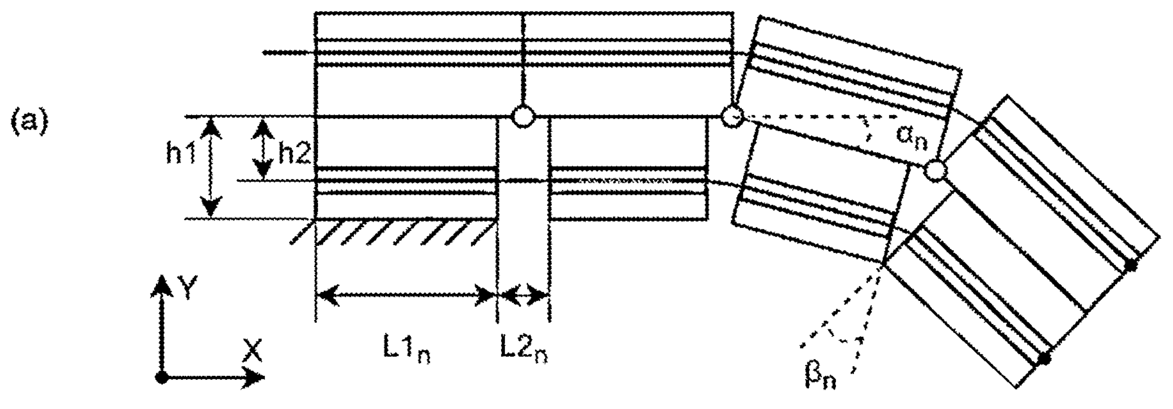
FIG. 11 depicts a two-dimensional model of the motion unit movement with one-dimensional rotational joints between adjacent movable members. The elongated motion unit is embodied as the one shown in FIGS. 3 and 10.
Figure 11:
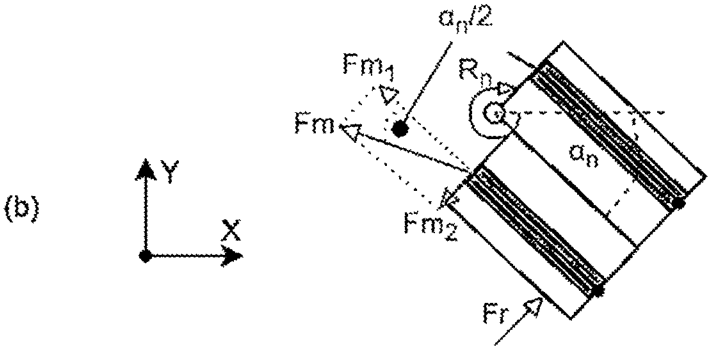

Using the mechanical equivalent model a two dimensional representation of the entire mechanism is developed. FIG. 11(*a*) shows the complete mechanism model. A free body diagram of a single element of the mechanism is analyzed as well. FIG. 11(*b*) shows the free body diagram of a single element of the mechanism.

n=Element n

L1n=Length of bottom element n

L2n=Length of bottom element n h1=Height of the elements h2=Distance between sandwich center and the actuation cable αn=Angle between element n and the following element βn=Maximal angle between element n and the following element Rn=Point of rotation Fr=Reaction force Fm=Motor force $$\sum T_{Rn}:\ Fm*\cos\left(\frac{\alpha_n}{2}\right)*h2+Fm*\sin\left(\frac{\alpha_n}{2}\right)*\frac{L2_n}{2}= Fr*\cos\left(\sum_{i=1}^{n}\alpha_i\right)*(R_{ny}-Fr_y)+Fr*\sin\left(\sum_{i=1}^{n}a_i\right)*(R_{nx}-Fr_x) \quad (1)$$

Equation 1 shows that the torque generated by Fm at Rn only depends on the parameter h2 and L2. The parameter L2 not only impacts the generated torque but also dictates the curled shape of the mechanism since it defines the end stop of each element. Hence, only the parameter h2 can be used to tune the mechanisms torque without compromising its trajectory. It is important to note that gravity was neglected due to the small weight of the mechanism in comparison to the acting forces.

The presented mechanism is classified as dynamic, since it is underactuated and driven by external forces. The more elements the mechanism is composed of, the more degrees of freedom are present. Based on the low weight and slow movements, it is expected that dynamic forces do not significantly contribute to the opening and closing force of the mechanism. Hence, only the quasi static model is used. An assumption is made to bypass the problem of the unknown trajectory of the system. Each rotational joint (Rn) is assumed to be locked, excepted for the one closest to the finger tip. When the mechanism curls it is assumed that the motion starts at the tip of the mechanism until the element hits its end stop. Then, all joints are assumed to be locked except the neighbouring one. It is assumed that the described pattern repeats until the mechanism is curled entirely. With this assumption the trajectory of the mechanism is defined throughout the complete movement, thus an analytical solution is enabled.

The assumption is based on equation 1, which shows that a constant reaction force at the tip of the mechanism requires an increasing torque, at the joints, proportional to the distance to the reaction force. Therefore, the joint which is closest to the reaction force requires the least torque to curl, thence it curls first.

It is assumed that the opening force and trajectory of the mechanism are the same, only the direction is inverted. This assumption is based on the mirrored geometry of the mechanism itself. Based on this assumption only half of the movement will be modelled and used for the dimensioning process.

Dimensioning of Mechanism

For the mechanism the following parameters are dimensioned: the total length of the motion unit, the amount of elements of the mechanism, the gap between each element, the distance of the cable to the backbone, the required stroke length of the cable and the force of the actuation. As a guidance throughout the dimensioning process, the requirement specifications and the analytical model are used.

In the implemented embodiment, the overall length of the mechanism is dimensioned based on the hand anthropometry of U.S. Army Personnel. It is expected that multiple lengths of the mechanism must be designed for a final product since the anthropometry of the human hand varies significantly to allow a universal design. Based on a worst case approach, 95th male percentile is chosen as a guidance for the overall length.

The force provided by the mechanism is depending on the actuation, the geometry of the motion unit itself and the distance of the cable to the backbone (h2 see FIG. 11). The diameter of the actuation's spool and h2 are selected based on the requirements. The requirement specification state that at the tip of the index finger a force of 12 N for closure and 29 N for opening must be present. The presented forces already include a safety factor of 1.2. In order to reach a trade-off between the force provided by the actuation and h2, the analytical model is used. Both values, force of the actuation and h2, are tuned until the weakest variant, variant three, reaches 58 N for small angles at the tip of the mechanism.

Hand Exoskeleton CAD Model

The hand exoskeleton CAD model is composed of three assemblies, the actuation, the glove and the mechanism. The root of the mechanism features the connector plate which holds three magnets, to connect to the glove, inside. The compliant backbone is located between the small elements. At the tip of the mechanism a double ring, for index and middle finger, is connected to the structure via a soft Y-shaped fabric. The fabric allows the double ring to slide on the main structure within a small range.

The gloves center piece is made out of a soft fabric. The fabric holds all components of the glove in position. At the wrist a cuff is integrated into the fabric contour which uses the reinforced slot to ensure a snug fit. A cable splitter is placed on top of the cuff to allow the actuation of multiple fingers at once. A reinforcing bracket is integrated at the forward end of the glove, the bracket serves as magnetic connector for the mechanism and as an interface to the user's hand. A slim strip of elastic fabric together with a small hook, closes the bracket and ensures a tight fit.

Implementation

Part Manufacturing

In the implemented embodiment according to the present example, fused deposition modelling (FDM), a type of 3D printing, is used to manufacture most parts. Additionally, standard parts and workshop equipment e.g. a drill press, are used. Since the hand exoskeleton is a wearable robotic device and is composed of fabric components, tailor equipment is used as well throughout the manufacturing process.

Fabric components of the hand exoskeleton require a precise cut contour. Therefore, the CAD model is used to print accurate paper stencils. The paper stencils are then fixated with needles on the fabric. A dressmaking scissor is used to carefully cut the fabric into the required shape.

Assembly

Techniques used in mechanical engineering such as fastening parts with screws, are only used for the assembly of the actuation. The usage of standard parts, in the actuation, enables fastening with screws. The glove and the mechanisms are exclusively assembled by stitching all parts together, using a conventional thread. Stitching as a joining technique allows a high integration of the fabric and rigid parts. Moreover, rigid and compliant parts can be joined reliably, while facilitating an overall soft structure. By using multiple layers of thread, high load bearing of the joints is achieved.

After the manufacturing of all components and the assembly, the prototype is finalized by connecting and programming the actuation. Each subassembly conforms to the 3D model. For testing purposes the sheath length of the actuation is dimensioned as 200 mm.

Range of Motion

The range of motion (RoM) defines the working space of the hand exoskeleton. The angles of the three joints MCP, PIP and DIP of the index finger are used to describe and compare the RoM. In order to determine the RoM of each mechanism's variant, the hand exoskeleton bench top is used. The bench top has a dummy hand with tracing markers on the index finger and a motion tracking system.

The RoM data for the verification of each mechanism's variant is recorded with the following actuation parameters: Stroke length 30 mm, speed 11.8 rpm. The action parameters are kept constant during the entire process. The validity of the measurements is ensured by tracking the motion of the dummy finger ten times for each variant.

The recorded trajectory data is post processed using a Python script. For the calculation of the mean trajectory of ten runs, resampling is necessary, since the closing motion among the runs is not synchronized. Hence, the data of each recorded run must be decoupled from the time and synchronized via a dimensionless variable. The decoupling of the data from the time stamp is achieved by using a Polynomial fit with a set number of sampling points. If the root mean square (RMS) error of the polynomial curve is smaller than the accuracy of the motion tracking algorithm, then the resampling does not result in an accuracy reduction.

The opening and closing time of the hand exoskeleton is measured at the actuator. The time required for the opening/closing stroke is assessed using a script, which communicates with the actuator via a serial port. A conservative accuracy of ±0.1 s is assumed, acknowledging a likely higher accuracy. The time of the opening stroke and the closing stroke are measured ten times each and the means are calculated. The mean time required to close the hand exoskeleton is 0.9 s±0.1 s and the mean time required to open the hand exoskeleton is 0.9 s±0.1 s.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. A hand exoskeleton comprising:

a hand- and/or wrist-wearable support having a portion configured to be connected in proximity to a metacarpophalangeal joint of a user; and an elongated motion unit operatively connected to, or stemming from, the hand- and/or wrist-wearable support, said elongated motion unit comprising:

a first, top layer of partial movable members comprising a first cavity along its entire length, a second, bottom layer of partial movable members comprising a second cavity along its entire length, a compliant layer sandwiched between said first, top layer and said second, bottom layer, the compliant layer running through the elongated motion unit and along the longitudinal axis of the elongated motion unit, a plurality of adjacent movable members located along the longitudinal axis of the motion unit, each of the movable members comprising a first and second cavity along its entire length, a first cable or wire running inside said first cavity and connected to the first, top layer, a second cable or wire running inside said second cavity and connected to the second, bottom layer, at least one finger support configured to locate two fingers of a user wearing the exoskeleton, the at least one finger support being disposed at one end of the elongated motion unit, one or more of the first layer and the second layer being connected at an end thereof to the at least one finger support.

2. The hand exoskeleton of claim 1, wherein said adjacent movable members comprise cutouts on a surface thereof, said cutouts being configured to permit bending of the elongated motion unit in a bending direction of a finger of a user.

3. The hand exoskeleton of claim 2, wherein said cutouts have different size features, including one or more of lengths and angles, from one of the movable members to another.

4. The hand exoskeleton of claim 1, wherein said elongated motion unit is configured as a monolithic structure.

5. The hand exoskeleton of claim 1, wherein the adjacent movable members are mechanically interconnected and independent.

6. The hand exoskeleton of claim 1, wherein said finger support is located on a distal portion of the elongated motion unit, and in proximity to the distal phalanges of a user wearing the exoskeleton.

7. The hand exoskeleton of claim 1, wherein the movable members have different lengths.

8. A hand exoskeleton system comprising:

a bi-directional actuating mechanism; and the hand exoskeleton of claim 1 operatively connected to the bi-directional actuating mechanism.

9. The hand exoskeleton system of claim 8, wherein the bi-directional actuating mechanism is selected from a list comprising a linear motor, a rotary motor, and a pneumatic actuator.

10. The hand exoskeleton device of claim 8, wherein the bi-directional actuating mechanism is a servomotor.

11. The hand exoskeleton device of claim 8, wherein the bi-directional actuating mechanism is operatively connected to one or more of said first cable or wire, the second cable or wire.

12. A hand exoskeleton comprising:

a hand- and/or wrist-wearable support having a portion configured to be connected in proximity to a metacarpophalangeal joint of a user; and an elongated motion unit operatively connected to, or stemming from, the hand- and/or wrist-wearable support, said elongated motion unit configured as a monolithic structure comprising a first cavity and a second cavity running inside the monolithic structure along its entire length, and a longitudinal cavity running along the longitudinal axis between the first cavity and the second cavity, the elongated motion unit comprising:

a plurality of adjacent movable members located along the longitudinal axis of the motion unit, a compliant element comprising a metal sheet inserted within said longitudinal cavity and running through said elongated motion unit along the longitudinal axis, a first cable or wire running inside said first cavity and connected to the elongated motion unit, a second cable or wire running inside said second cavity and connected to the elongated motion unit, and at least one finger support configured to locate two fingers of a user wearing the hand exoskeleton, wherein said motion unit is connected at one end to the finger support.

13. The hand exoskeleton of claim 12, wherein the adjacent movable members are mechanically interconnected and independent.

14. The hand exoskeleton of claim 12, wherein said adjacent movable members comprise cutouts on a surface thereof, said cutouts being configured to permit bending of the elongated motion unit in a bending direction of a finger of a user.

15. The hand exoskeleton of claim 14, wherein said cutouts have different size features, including one or more of lengths and angles, from one of the movable members to another.

16. The hand exoskeleton of claim 12, wherein said finger support is located on a distal portion of the elongated motion unit, and in proximity to the distal phalanges of a user wearing the exoskeleton.

17. The hand exoskeleton of claim 12, wherein the movable members have different lengths.

18. A hand exoskeleton system comprising:

a bi-directional actuating mechanism; and the hand exoskeleton of claim 13 operatively connected to the bi-directional actuating mechanism.

19. The hand exoskeleton system of claim 18, wherein the bi-directional actuating mechanism is selected from a list comprising a linear motor, a rotary motor, and a pneumatic actuator.

20. The hand exoskeleton device of claim 18, wherein the bi-directional actuating mechanism is a servomotor.

21. The hand exoskeleton device of claim 18, wherein the bi-directional actuating mechanism is operatively connected to one or more of said first cable or wire, the second cable or wire.

* * * * *